(12) United States Patent
Cowan et al.

(10) Patent No.: US 10,143,850 B2
(45) Date of Patent: *Dec. 4, 2018

(54) SYSTEMS AND METHODS FOR IMPLANTABLE LEADLESS TISSUE STIMULATION

(71) Applicant: EBR Systems, Inc., Sunnyvale, CA (US)

(72) Inventors: Mark W. Cowan, San Jose, CA (US); Richard E. Riley, Palo Alto, CA (US); Axel F. Brisken, Fremont, CA (US); Debra S. Echt, Tiburon, CA (US)

(73) Assignee: EBR Systems, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/250,897

(22) Filed: Aug. 29, 2016

(65) Prior Publication Data

US 2016/0367823 A1    Dec. 22, 2016

Related U.S. Application Data

(60) Continuation of application No. 13/922,937, filed on Jun. 20, 2013, now Pat. No. 9,452,286, which is a (Continued)

(51) Int. Cl.
*A61N 1/37*    (2006.01)
*A61N 1/378*    (2006.01)
(Continued)

(52) U.S. Cl.
CPC ........... *A61N 1/3787* (2013.01); *A61N 1/326* (2013.01); *A61N 1/36* (2013.01); *A61N 1/3604* (2017.08);
(Continued)

(58) Field of Classification Search
CPC .................................................. A61N 1/37217
See application file for complete search history.

(56) References Cited

U.S. PATENT DOCUMENTS 3,486,506 A    12/1969    Michel
3,522,811 A    8/1970    Seymour et al.
(Continued)

FOREIGN PATENT DOCUMENTS

DE    4330680 A1    3/1995
WO    WO-2007149936 A2    12/2007
WO    WO-2007149936 A3    10/2008

OTHER PUBLICATIONS

Heckman et al., "Acceleration of tibial fracture-healing by non-invasive, low-intensity pulsed ultrasound" The Journal of Bone and Joint Surgery, vol. 76, Issue 1, pp. 26-34, 1994.
(Continued)

*Primary Examiner* — Eric D. Bertram
(74) *Attorney, Agent, or Firm* — Wilson Sonsini Goodrich & Rosati

(57) ABSTRACT

Systems and methods are disclosed to stimulate tissue to treat medical conditions involving tissues such as the bone, spine, stomach, nerves, brain and the cochlea. The disclosed invention uses electrical stimulation of the tissue, where vibrational (or acoustic) energy from a source is received by an implanted device and converted to electrical energy and the converted electrical energy is used by implanted electrodes to stimulate the pre-determined tissue sites. The vibrational energy is generated by a controller-transmitter, which could be either implanted or located externally. The vibrational energy is received by a receiver-stimulator, which could be located at or close to the stimulation site.

7 Claims, 22 Drawing Sheets

Related U.S. Application Data continuation of application No. 13/292,854, filed on Nov. 9, 2011, now Pat. No. 8,494,644, which is a division of application No. 11/764,561, filed on Jun. 18, 2007, now Pat. No. 8,078,283, application No. 15/250,897, which is a continuation of application No. 13/007,419, filed on Jan. 14, 2011, now Pat. No. 8,494,642, which is a division of application No. 11/764,574, filed on Jun. 18, 2007, now Pat. No. 7,899,542, application No. 15/250,897, which is a continuation of application No. 13/008,521, filed on Jan. 18, 2011, now Pat. No. 8,494,637, which is a division of application No. 11/764,583, filed on Jun. 18, 2007, now Pat. No. 7,899,541, application No. 15/250,897, which is a continuation of application No. 13/008,433, filed on Jan. 18, 2011, now Pat. No. 8,494,643, which is a division of application No. 11/764,592, filed on Jun. 18, 2007, now Pat. No. 7,894,907, application No. 15/250,897, which is a continuation of application No. 13/007,432, filed on Jan. 14, 2011, now Pat. No. 8,494,639, which is a division of application No. 11/764,602, filed on Jun. 18, 2007, now Pat. No. 7,894,904, application No. 15/250,897, which is a continuation of application No. 13/008,462, filed on Jan. 18, 2011, now Pat. No. 8,498,715, which is a division of application No. 11/764,611, filed on Jun. 18, 2007, now Pat. No. 7,894,910.

(60) Provisional application No. 60/805,314, filed on Jun. 20, 2006, provisional application No. 60/805,315, filed on Jun. 20, 2006, provisional application No. 60/805,316, filed on Jun. 20, 2006, provisional application No. 60/805,319, filed on Jun. 20, 2006, provisional application No. 60/805,320, filed on Jun. 20, 2006, provisional application No. 60/805,323, filed on Jun. 20, 2006.

(51) Int. Cl.
*A61N 1/32* (2006.01)
*A61N 1/372* (2006.01)
*A61N 1/375* (2006.01)
*A61N 1/36* (2006.01)

(52) U.S. Cl.
CPC ..... *A61N 1/36007* (2013.01); *A61N 1/36021* (2013.01); *A61N 1/36036* (2017.08); *A61N 1/36071* (2013.01); *A61N 1/3756* (2013.01); *A61N 1/37217* (2013.01); *A61N 1/37288* (2013.01)

(56) References Cited

U.S. PATENT DOCUMENTS

| | | |
|---|---|---|
| 3,751,605 A | 8/1973 | Michelson |
| 3,835,833 A | 9/1974 | Limoge |
| 3,943,936 A | 3/1976 | Rasor et al. |
| 4,026,304 A | 5/1977 | Levy |
| 4,333,469 A | 6/1982 | Jeffcoat et al. |
| 4,400,590 A | 8/1983 | Michelson |
| 4,530,360 A | 7/1985 | Duarte |
| 4,690,144 A | 9/1987 | Rise et al. |
| 4,819,647 A | 4/1989 | Byers et al. |
| 5,188,104 A | 2/1993 | Wernicke et al. |
| 5,193,540 A | 3/1993 | Schulman et al. |
| 5,215,086 A | 6/1993 | Terry, Jr. et al. |
| 5,251,634 A | 10/1993 | Weinberg |
| 5,282,468 A | 2/1994 | Klepinski |
| 5,309,898 A | 5/1994 | Kaufman et al. |
| 5,330,515 A | 7/1994 | Rutecki et al. |
| 5,358,514 A | 10/1994 | Schulman et al. |
| 5,405,367 A | 4/1995 | Schulman et al. |
| 5,411,535 A | 5/1995 | Fujii et al. |
| 5,441,527 A | 8/1995 | Erickson et al. |
| 5,496,256 A | 3/1996 | Bock et al. |
| 5,531,778 A | 7/1996 | Maschino et al. |
| 5,547,459 A | 8/1996 | Kaufman et al. |
| 5,556,372 A | 9/1996 | Talish et al. |
| 5,716,377 A | 2/1998 | Rise et al. |
| 5,752,924 A | 5/1998 | Kaufman et al. |
| 5,782,798 A | 7/1998 | Rise |
| 5,814,089 A | 9/1998 | Stokes et al. |
| 5,876,425 A * | 3/1999 | Gord .................. A61N 1/36032 607/33 |
| 5,938,690 A | 8/1999 | Law et al. |
| 6,002,965 A | 12/1999 | Katz et al. |
| 6,016,449 A | 1/2000 | Fischell et al. |
| 6,027,456 A | 2/2000 | Feler et al. |
| 6,037,704 A | 3/2000 | Welle |
| 6,141,588 A | 10/2000 | Cox et al. |
| 6,231,528 B1 | 5/2001 | Kaufman et al. |
| 6,322,527 B1 | 11/2001 | Talish |
| 6,366,816 B1 | 4/2002 | Marchesi |
| 6,427,086 B1 | 7/2002 | Fischell et al. |
| 6,505,074 B2 | 1/2003 | Boveja et al. |
| 6,615,081 B1 | 9/2003 | Boveja |
| 6,622,038 B2 | 9/2003 | Barrett et al. |
| 6,622,041 B2 | 9/2003 | Terry et al. |
| 6,622,047 B2 | 9/2003 | Barrett et al. |
| 6,652,473 B2 | 11/2003 | Kaufman et al. |
| 6,654,638 B1 | 11/2003 | Sweeney |
| 6,671,559 B2 | 12/2003 | Goldsmith et al. |
| 6,684,105 B2 | 1/2004 | Cohen et al. |
| 6,735,475 B1 | 5/2004 | Whitehurst et al. |
| 6,748,276 B1 | 6/2004 | Daignault, Jr. et al. |
| 6,879,859 B1 | 4/2005 | Boveja |
| 6,889,094 B1 | 5/2005 | Kuzma et al. |
| 7,003,350 B2 | 2/2006 | Denker et al. |
| 7,010,351 B2 | 3/2006 | Firlik et al. |
| 7,013,177 B1 | 3/2006 | Whitehurst et al. |
| 7,047,078 B2 | 5/2006 | Boggs et al. |
| 7,894,904 B2 * | 2/2011 | Cowan ................. A61N 1/0531 607/45 |
| 7,894,907 B2 * | 2/2011 | Cowan .................... A61N 1/08 607/46 |
| 7,899,541 B2 * | 3/2011 | Cowan .................... A61N 1/05 607/40 |
| 7,899,542 B2 * | 3/2011 | Cowan ............... A61N 1/37217 607/46 |
| 8,078,283 B2 * | 12/2011 | Cowan ................... A61N 1/326 607/51 |
| 8,494,637 B2 * | 7/2013 | Cowan .................... A61N 1/05 607/40 |
| 8,494,639 B2 * | 7/2013 | Cowan .................. A61N 1/0531 607/45 |
| 8,494,642 B2 * | 7/2013 | Cowan ............... A61N 1/37217 607/46 |
| 8,494,643 B2 * | 7/2013 | Cowan .................... A61N 1/08 607/46 |
| 8,494,644 B2 * | 7/2013 | Cowan ................... A61N 1/326 607/51 |
| 8,494,693 B2 * | 7/2013 | Murphy ............... G05D 1/0676 340/947 |
| 8,498,715 B2 * | 7/2013 | Cowan ............... A61N 1/36032 607/57 |
| 9,452,286 B2 * | 9/2016 | Cowan .................. A61N 1/326 |
| 2004/0172083 A1 * | 9/2004 | Penner ................. A61B 5/0031 607/35 |
| 2006/0136004 A1 | 6/2006 | Cowan et al. |

(56) References Cited

U.S. PATENT DOCUMENTS

2007/0293912 A1    12/2007    Cowan et al.
2013/0282070 A1    10/2013    Cowan et al.

OTHER PUBLICATIONS

International search report and written opinion dated Aug. 8, 2008 for PCT/US2007/071693.
Notice of allowance dated May 23, 2013 for U.S. Appl. No. 13/292,854.
Notice of allowance dated May 24, 2016 for U.S. Appl. No. 13/922,937.
Notice of allowance dated Aug. 10, 2011 for U.S. Appl. No. 11/764,561.
Office action dated Mar. 3, 2013 for U.S. Appl. No. 13/292,854.
Office action dated Mar. 11, 2011 for U.S. Appl. No. 11/764,561.
Office action dated Mar. 29, 2016 for U.S. Appl. No. 13/922,937.
Office action dated May 24, 2010 for U.S. Appl. No. 11/764,561.
Office action dated May 29, 2009 for U.S. Appl. No. 11/764,561.
Office action dated Jun. 17, 2015 for U.S. Appl. No. 13/922,937.
Office action dated Oct. 28, 2009 for U.S. Appl. No. 11/764,561.
Office action dated Oct. 31, 2014 for U.S. Appl. No. 13/922,937.
Office action dated Nov. 3, 2010 for U.S. Appl. No. 11/764,561.
Office action dated Nov. 12, 2008 for U.S. Appl. No. 11/764,561.
Office action dated Nov. 21, 2012 for U.S. Appl. No. 13/292,854.

\* cited by examiner

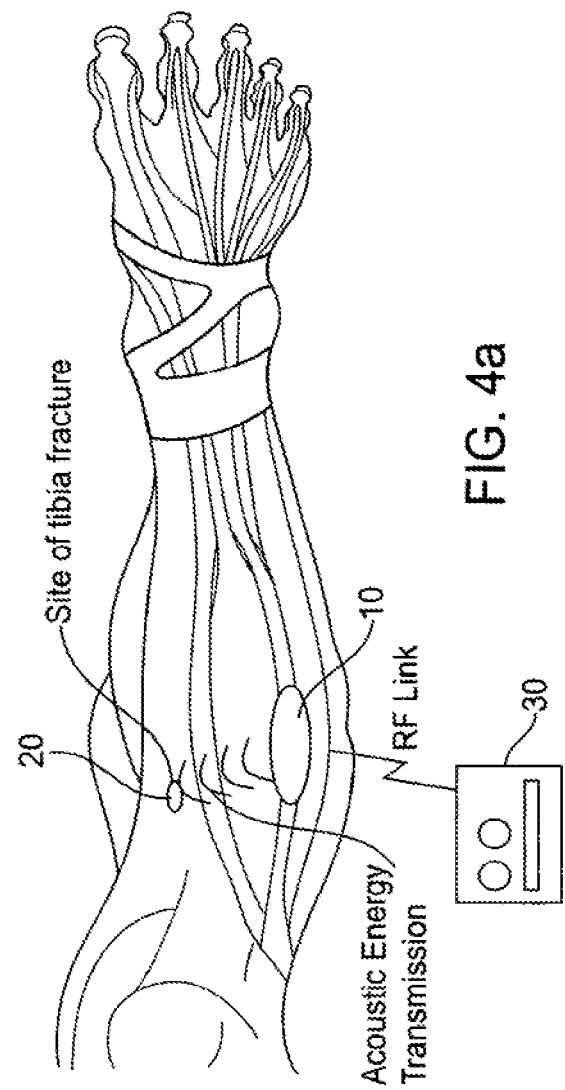

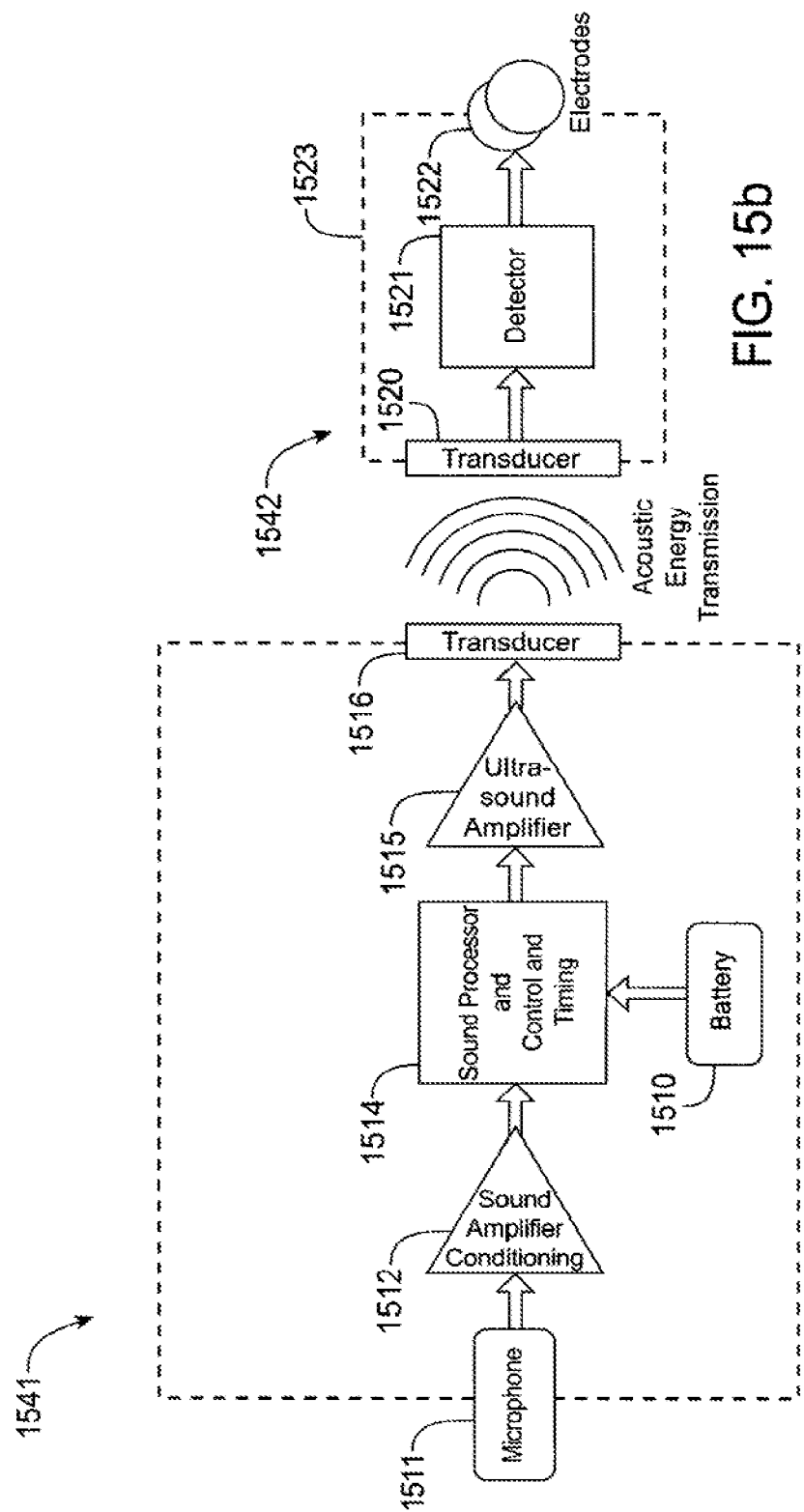

SYSTEMS AND METHODS FOR IMPLANTABLE LEADLESS TISSUE STIMULATION

CROSS REFERENCE TO RELATED APPLICATIONS

This application is a continuation of U.S. patent application Ser. No. 13/922,937, filed Jun. 20, 2013 (now U.S. Pat. No. 9,452,286), which is a continuation of U.S. patent application Ser. No. 13/292,854, filed Nov. 9, 2011, (now U.S. Pat. No. 8,494,644) which is a divisional of U.S. patent application Ser. No. 11/764,561, filed Jun. 18, 2007, (now U.S. Pat. No. 8,078,283), which claims the benefit of U.S. Provisional Application No. 60/805,314, filed Jun. 20, 2006; this application is also a continuation of U.S. patent application Ser. No. 13/007,419, filed Jan. 14, 2011 (now U.S. Pat. No. 8,494,642), which is a divisional of U.S. patent application Ser. No. 11/764,574, filed Jun. 18, 2007 (now U.S. Pat. No. 7,899,542), which claims the benefit of U.S. Provisional Application No. 60/805,315, filed Jun. 20, 2006; this application is also a continuation of Ser. No. 13/008,521, filed Jan. 18, 2011 (now U.S. Pat. No. 8,494,637), which is a divisional of U.S. patent application Ser. No. 11/764,583, filed Jun. 18, 2007 (now U.S. Pat. No. 7,899,541), which claims the benefit of U.S. Provisional No. 60/805,316, filed Jun. 20, 2006; this application is also a continuation of U.S. patent application Ser. No. 13/008,433, filed Jan. 18, 2011 (now U.S. Pat. No. 8,494,643), which is a divisional of U.S. patent application Ser. No. 11/764,592, filed Jun. 18, 2007 (now U.S. Pat. No. 7,894,907), which claims the benefit of U.S. Provisional Application No. 60/805,319, filed Jun. 20, 2006; this application is also a continuation of U.S. patent application Ser. No. 13/007,432, filed Jan. 14, 2011 (now U.S. Pat. No. 8,494,639), which is a divisional of U.S. patent application Ser. No. 11/764,602, filed Jun. 18, 2007 (now U.S. Pat. No. 7,894,904), which claims the benefit of U.S. Provisional Application No. 60/805,320, filed Jun. 20, 2006; and this application is a continuation of U.S. patent application Ser. No. 13/008,462, filed Jan. 18, 2011 (now U.S. Pat. No. 8,498,715), which is a divisional of U.S. patent application Ser. No. 11/764,611, filed Jun. 18, 2007 (now U.S. Pat. No. 7,894,910), which claims the benefit of U.S. Provisional No. 60/805,323, filed Jun. 20, 2006; the full disclosures of which are incorporated herein by reference.

BACKGROUND OF THE INVENTION

1. Field of the Invention

The systems and methods of this invention relate to electrical tissue stimulation treatments using implantable devices. Specifically, the present invention relates to systems and methods for providing such stimulation without the use of conventional lead/electrode systems for stimulating tissues such as, bone, brain, spine, stomach, nerve, and cochlea for therapeutic purposes.

2. Description of the Background Art

Electrical stimulation of body tissues is used for treatment of both chronic and acute medical conditions. Perhaps the best known medical application of electrical stimulation is that used to initiate a heart beat by stimulating cardiac tissue for the treatment of arrhythmias. Among several other examples, direct muscle stimulation is used to initiate contraction of functional muscles in paraplegics; peripheral muscle stimulation is known to accelerate healing of strains and tears; bone stimulation is likewise indicated to increase the rate of bone regrowth and repair in fractures; and nerve stimulation is used to alleviate chronic pain. Furthermore, there is encouraging research in the use of electrical stimulation to treat a variety of nerve and brain conditions, such as essential tremor, Parkinson's disease, migraine headaches, functional deficits due to stroke, and epileptic seizures. Another area where electrical stimulation is used to treat a medical condition is the electrical stimulation of the cochlea of the ear and to cochlear nerves and to regions proximal to cochlear nerves of the ear as a treatment for hearing loss.

For electrical tissue stimulation, generally, the system comprises a transmitter or a controller and a stimulator. Additionally, there may be a programmer that communicates with the transmitter and exchanges stimulation parameters. The transmitter and the stimulator may be external or implanted. In the embodiment where leads connect the transmitter and the stimulator, electrodes are present on the leads and are in contact with the tissue that is to be stimulated. Understandably, there are variations in the details of the devices, depending on the tissue to be stimulated. Various devices and arrangements that are currently used for stimulating different tissues and their shortcomings are described below.

In current practice, implanted electrical energy sources and electrode/lead wire systems are typically used to directly stimulate tissue at the desired site. Such implanted electrode/lead wires exhibit significant problems, such as infection, lead failure, and electrode/lead dislodgement. If the leads were externalized, then the entry/exit site in the skin must be carefully managed to avoid infection. Various approaches for different tissue stimulations that are prevalent, and their shortcomings, are described below.

Bone Stimulation

Bone stimulation is used to increase the rate of bone regrowth, repair, fusion of bones or bone grafts. Commonly implanted devices utilizing electrical stimulation for treatment in bone fusion are made by such companies as Biomet (Electro-Biology, Inc. (EBI)). Similarly, ultrasound energy has been used as a noninvasive therapeutic healing application in bone treatments, such as in the Exogen Bone Healing System made by Smith&Nephew.

Electrical bone growth stimulation (EBGS) generally refers to the treatment of bone fusion or repair using electrical current (direct current or alternating current). Currently, invasive use of these devices involves surgical implantation of a current generator in an intramuscular or subcutaneous space, while an electrode is implanted within the fragments of bone or bone graft at the bone fusion site. Limited by battery utilization, the implantable device typically remains functional for six to nine months after implantation; alternatively, it can be adapted to be rechargeable. Although the current generator is removed in a second surgical procedure when stimulation is completed, the electrode may or may not be removed. Noninvasive approaches that apply an electrical or electro-magnetic field transcutaneously to the bone area via externally worn devices are also available. Ultrasonic bone growth stimulation (UBGS) generally refers to the treatment of bone fusion and repair using low-intensity ultrasound as an energy source and the ultrasound energy is externally applied. In noninvasive electrical applications, electrical devices require patient interaction to apply and remove electrodes. Compliance with noninvasive EBGS and UBGS is often an issue because it requires the patient to apply the therapy at a prescribed regimen and intensity. Patients may not keep batteries charged, may not comply with instructions, may fail to wear electrodes for required durations, or may adjust intensities inappropriately for the electrical bone stimulation therapy or ultrasound therapy application to be effective.

EBGS is used as an adjunct to spinal fusion surgery, with or without associated devices such as cages or screws to enhance the chances of obtaining a solid spinal fusion. EBGS has also been used as a treatment of failed spinal fusion surgery (i.e., salvage therapy). Pedicle screws and interbone cages are devices used to facilitate fusion. The role of electrical stimulation of the spine for instrumented fusions, and also in patients not considered at high risk for fusion failure, is still emerging. EBGS may be considered medically necessary as an adjunct to spinal fusion surgery for patients with risk factors for failed fusion, e.g. diabetes, renal disease, smoking, alcoholism, etc.

EBGS or UBGS is also used in appendicular skeleton for the treatment of fracture non-unions. A nonunion is considered to be established when after a period of time, since injury at the fracture site shows no visibly progressive signs of healing. Complicated variables are present in fractures, e.g., degree of soft tissue damage, alignment of the bone fragments, vascularity, and quality of the underlying bone stock. Delayed union refers to a decelerating bone healing process, as identified in serial x-rays. (In contrast, nonunion serial x-rays show no evidence of healing.) When lumped together, delayed union and nonunion are sometimes referred to as "un-united fractures."

In the appendicular skeleton, EBGS or UBGS has been used primarily to treat tibial fractures. According to orthopedic anatomy, the skeleton consists of long bones, short bones, flat bones, and irregular bones. Long bones act as levers to facilitate motion, while short bones function to dissipate concussive forces. Short bones include those composing the carpus and tarsus. Flat bones, such as the scapula or pelvis provide a broad surface area for attachment of muscles. Thus the metatarsal is considered a long bone, while the scaphoid bone of the wrist is considered a short bone. Both the metatarsals and scaphoid bones are at a relatively high risk of nonunion after a fracture.

All bones are composed of a combination of cortical and trabecular (also called cancellous) bone. Cortical bone is always located on the exterior of the bone, while the trabecular bone is found in the interior. Each bone, depending on its physiologic function, has a different proportion of cancellous to trabecular bone. However, at a cellular level, both bone types are composed of lamellar bone and cannot be distinguished microscopically.

Devices to provide EBGS may be noninvasive, with electrodes placed on the skin surface over the area of the bone to be treated. These external EBGS systems are similar to transcutaneous electrical nerve stimulators (TENS). Electrodes on the skin surface are connected to a manually adjusted stimulation controller, typically powered by batteries, which is worn by the patient on a harness or belt. In some cases it is more advantageous to implant all or part of the EBGS device. In implantable systems, the electrodes, constructed on lead wires, are placed directly on the bone, in the area of the bone, or within bone graft material. These leads are then externalized to the skin surface and connected to an external stimulation controller or more typically are arranged in a subcutaneous location where an implantable stimulation controller is subcutaneously implanted and connected to the leads. The invention described in this patent application pertains to EBGS devices in which at least one portion providing direct electrical stimulation to the bone, in the area of the bone, or within bone graft material is either permanently or temporarily implanted. The other portion, the stimulation controller, may or may not be implanted. Devices to provide UBGS are noninvasive systems: the ultrasound transmitter is placed on the skin, coupled to the body using gel, and held over the targeted bone region for the prescribed duration with a prescribed low-intensity ultrasound applied for the treatment duration.

In current practice, implanted electrical energy sources and electrode/lead wire systems are typically used to directly stimulate bone at the site of repair. Such implanted electrode/lead wires exhibit significant problems, such as infection, lead failure, and electrode/lead dislodgement. In certain applications, e.g., EBGS for treatment of bone fusions, leads are implanted at the time of bone repair surgery and left unconnected, awaiting determination of whether the bone will fuse without the aid of electrical stimulation. If the leads were externalized, then the entry/exit site in the skin must be carefully managed to avoid infection. In case of non-fusion, the leads are then connected to a stimulation controller/pulse generator. If the stimulation controller is implanted, this involves yet another procedure.

The methods and apparatus of the current invention utilize vibrational energy, particularly at ultrasonic frequencies, to overcome many of the limitations of currently known solutions for EBGS, by achieving a bone stimulation capability without the use of leads connected to a stimulation controller/pulse generator. The invention described in this patent application pertains also to UBGS devices and devices combining both UBGS and EBGS function wherein the ultrasound stimulation generator or the combined ultrasound generator and electrical stimulation controller may or may not be implanted.

Spine Stimulation

Electrical stimulation of spinal nerve roots, the spinal cord, and/or other nerve bundles in the region of the spine, for the purpose of chronic pain management, has been actively practiced since the 1960s. Application of an electrical field to nerve tissue in the spine (i.e., spinal nerve roots and spinal cord bundles) is known to effectively interfere with the transmission of pain signals to the brain. These applications are done today both with externally applied devices and implanted devices. Applying specific electrical pulses to spinal nervous tissue or to peripheral nerve fibers that corresponds to regions of the body afflicted with chronic pain can induce paresthesia, or a subjective sensation of numbness or tingling, or can in effect block pain transmission to the brain from the pain-afflicted regions. Depending on the individual patient, paresthesia can effectively "mask" certain pain sensations to the brain. Treatment regimens and targeted spinal locations are known in related art through use of current, common stimulation devices and methods. Commonly implanted devices for spinal nerve stimulation are made by such companies as Medtronic, Advanced Neuromodulation Systems, Advanced Bionics, and others.

The spine is an anatomical structure that consists of bones (vertebrae), cartilage (discs), and the spinal cord (a nervous system structure that generally bundles or collects various nerves connecting peripheral areas of the body to the brain). The spine is divided into five regions: (i) cervical (neck), (ii) thoracic (mid-back), (iii) lumbar (lower back), (iv) sacrum, and (v) coccyx (tailbone). The peripheral nervous system refers to the cervical, thoracic, lumbar, and sacral nerve trunks leading away from the spine to all regions of the body. The peripheral nervous system also includes cranial nerves. Pain signals travel between the brain and to other regions of the body using this network of nerves that all travel along the spine as part of the spinal cord.

Transcutaneous electrical nerve stimulation (TENS) is a well known medical treatment used primarily for symptomatic relief and management of chronic intractable pain and as an adjunctive treatment in the management of post surgical and post traumatic acute pain. TENS involves the application of electrical pulses to the skin of a patient, which pulses are generally of a low frequency and are intended to affect the nervous system in such a way as to suppress the sensation of pain, in the area that the electrodes are applied. This typically would be indicated for use in acute or chronic injury or otherwise used as a protective mechanism against pain. Typically, two electrodes are secured to the skin at appropriately selected locations. Mild electrical impulses are then passed into the skin through the electrodes to interact with the nerves lying thereunder. As a symptomatic treatment, TENS has proven to effectively reduce both chronic and acute pain of patients.

Spinal Cord Stimulation (SCS) generally refers to treatments for a variety of medical conditions that apply electrical stimulation directly on nerves, nerve roots, nerve bundles, tissue or regions of the spine. Currently available stimulator systems for SCS are fully implanted electronic devices placed subcutaneously under the skin and connected via insulated metal lead(s) to electrodes which are invasively inserted into or onto the nerves or close to the nerves or spinal cord region. A commonly implanted SCS system contains a battery to power the system. Some implanted SCS systems use an RF wireless connection instead of a battery to power the implanted device. In these RF systems, a receiver device is implanted subcutaneously and a transmitter is worn on the outside of the body. The antenna are tuned to each other and aligned such that control information and power is transmitted to the receiver, which then directs the electrical impulses to the electrodes through the leads. The external transmitter contains batteries to power the transmission. All systems have the capability to externally adjust settings of the implanted system through a programming device.

In SCS and TENS systems, electrical energy is delivered through lead wires to the electrodes. For SCS, implanted electrodes are positioned external to a patient's dura layer (epidural), a structure that surrounds the spinal cord. SCS uses the implanted electrodes to deliver a variety of stimulation modalities with the electric pulse waveform defined by a plurality of variables, including: pulse width, pulse frequency (Hz) or duty cycle, amplitude (V), and sometimes waveform shape (e.g. mono-phasic or bi-phasic).

SCS is used for treatment of headache, migraine headache, or facial pain by stimulating spinal cord including the trigeminal ganglion or ganglia, a trigeminal nerve(s), a branch(es) of a trigeminal nerve(s) (e.g., an ophthalmic nerve(s), a maxillary nerve(s), and/or a mandibular nerve(s)), or a branch(es) of any of these neural structures.

SCS is used for the treatment of chronic pelvic pain due to such conditions as lumbosacral radiculitis, lumbosacral radiculopathy, lumbosacral plexitis, lumbosacral plexopathy, vulvadynia, coccygodynia, peripheral neuritis, and peripheral neuropathy, by applying stimulation to the epidural space of the sacrum on or near selected sacral nerve roots.

SCS is used for chronic pain associated with injury to the spine such as herniated discs or compression fractures. SCS is also used for treating severe chronic pain of a nonspecific origin. Stimulation of nerve tissue in a variety of spinal areas is known to reduce symptoms and enhance the quality of life in patients with chronic pain.

As described above, TENS and SCS devices are battery-powered electronic devices either used transcutaneously (TENS) or implanted (SCS) and connected via insulated metal lead(s) to electrodes which are either placed on the skin (TENS) over the spine or implanted into the dura or epidural layer of the spine (SCS). The implanted electrodes for SCS are positioned on leads that are placed percutaneously, through needle punctures, or through minimally invasive surgical procedures such laminectomy methods, or through direct surgical access to position the electrodes into epidural regions of the spine. Multiple electrodes typically between 4 and 16 are available on the lead and are positioned in the region that is targeted for electrical stimulation. The implanted leads are then subcutaneously tunneled to the pulse generator (also referred to as a controller) that is implanted in a subcutaneous pocket. The use of these lead wires is associated with significant problems such as complications due to infection, lead failure, lead migration, and electrode/lead dislodgement.

Many attempts to overcome the complications and limitations imposed by the use of electrical leads have been reported. For example, self-contained implantable microstimulators and remotely powered microstimulators have been described; however each approach suffers from some significant limitation. A self-contained microstimulator must incorporate a battery or some other power supply; this imposes constraints on size, device lifetime, available stimulation energy, or all three. Due to high use or high energy requirements of the therapeutic stimulation some SCS devices contain recharageable batteries or are powered remotely with an RF coupling to the controller.

For leadless solutions in other similar stimulation applications, remotely powered devices have previously utilized either radiofrequency (RF) or electromagnetic transformer power transmission. RF energy transmission, unless the transmitting and receiving antennae are placed in close proximity, suffers from inefficiency and limited safe power transfer capabilities, limiting its usefulness in applications where recharging or stimulation must be accomplished at any significant depth (>1-2 cm) within the body, in particular where it is desired to permanently implant both the transmitter and receiver-stimulator. Electromagnetic coupling can more efficiently transfer electrical power, and can safely transfer higher levels of power (devices with capacity in excess of 20 Watts have been produced) but again relies on close proximity between transmitting and receiving coils, or the utilization of relatively large devices for deeper (5-8 cm maximum) implantation.

GI Stimulation

Electrical stimulation of the gastrointestinal system or gastrointestinal tract for the purpose of controlling gastrointestinal activity has been known and actively practiced for several decades. Application of an electrical field between electrodes to gastrointestinal tissue is known to affect the motility and electromotor conduct of the gastric tract; for example, it has been used in the treatment of eating disorders (e.g., obesity, thinness, bulimia, anorexia). For example, applying specific electrical pulses to the selected areas of the stomach can induce a sense of satiety. Disturbances in electromotor activity in diabetic gastroparesis, reflux in the upper digestive tract, and numerous other gastro-enterological functional pathologies can be observed with electrophysiologic sensing and also treated with application of electrical stimulation. Electrical stimulation of other locations in the tract can induce voiding or can be used as a treatment for gastric reflux. These applications are currently practiced using both implanted and externally applied devices.

Depending on the individual patient, gastrointestinal stimulation can effectively modify signal pathways along the tract and thus provide relief of symptoms or control of bodily function. Treatment regimens and targeted gastrointestinal tissue locations are known in related art through use of current, common stimulation devices and methods. Currently, implanted devices for gastrointestinal tissue stimulation are made by companies such as IntraPace and Transneuronix.

The gastrointestinal system is essentially a long tube running from the mouth to the anus consisting of four main sections including the oesophagus, the stomach, the small intestines, and the large intestines. These specialized sections are capable of digesting material place in the mouth and extracting components useful to the body as the material passes through the system. Material that can not be used or that has been processed is expelled from the end of the tube at the anus. The system is under hormonal control, with the presence of food in the mouth triggering off a cascade of hormonal actions; when there is food in the stomach, different hormones activate acid secretion, increased gut motility, enzyme release etc. The stomach is a 'j'-shaped organ, with two openings—the esophageal and the duodenal, and four regions—the cardia, fundus, body and pylorus. Each region performs different functions; the fundus collects digestive gases, the body secretes pepsinogen and hydrochloric acid, and the pylorus is responsible for mucus, gastrin and pepsinogen secretion. The body uses this arrangement to process food and supply nutrients to the system.

In one early application of electrical gastrointestinal tissue stimulation, an electrode was passed down the esophagus to the stomach and electrical stimulation applied between the electrode and an electrode placed on the patient's abdomen. This induced peristaltic activity within the system. This was an external application of the electrical stimulation system. More recently, the concept has been extended to apply an implantable system into the stomach either as a self-contained stimulator or with electrodes on leads attached to the stomach and then connected to a subcutaneous implanted pulse generator. These systems have been found useful in treatment of obesity both for improving motility in patients and for providing a feeling of satiety to reduce intake.

In the context of this patent application, Gastrointestinal Tissue Stimulation (GTS) refers to treatments for a variety of medical conditions that apply electrical stimulation directly to gastrointestinal tissues. Currently available stimulator systems for GTS are fully implanted electronic devices placed within the stomach or placed subcutaneously under the skin and connected via insulated metal lead(s) to electrodes which are invasively inserted into, around, or onto gastrointestinal tissue. An implanted GTS system contains a battery to power the system. Some implanted GTS systems use an RF wireless connection instead of a battery to power the implanted device. In these RF systems, a receiver device is implanted subcutaneously and a transmitter is worn on the outside of the body. The antenna are tuned to each other and aligned such that control information and power is transmitted to the receiver and then directs the electrical impulses to the electrodes through the leads. The external transmitter contains batteries to power the transmission. All systems have the capability to externally adjust settings of the implanted system through a programming device.

In some GTS systems, electrical energy is delivered through lead wires to the electrodes; in other applications, the self-contained devices incorporate a battery with electrodes disposed on the outer surfaces of the device. For GTS, implanted electrodes are positioned on, around, or in close proximity to the gastrointestinal tissue to be stimulated. GTS uses the implanted electrodes to deliver a variety of stimulation modalities for propagation along the gastrointestinal tissue with the electric pulse waveform defined by a plurality of variables, including: pulse width, pulse frequency (Hz) or duty cycle, amplitude (V), and waveform shape (e.g., monophasic or bi-phasic).

GTS is used for treatment of motor disorders of the stomach, such as duodenogastric and gastroesophageal refluxes and relapsing duodenal peptic disorders (ulcer or phlogosis); and for treating obesity and other syndromes related to motor disorders of the stomach.

As described above, GTS devices are battery-powered electronic devices implanted and often connected via insulated metal lead(s) to electrodes which are either placed on the stomach or in the stomach or otherwise within or on the gastrointestinal tissues selected for stimulation. The implanted electrodes for GTS are positioned on leads that may be placed percutaneously, through needle punctures, or through minimally invasive surgical procedures such as laparoscopic methods, or through direct surgical access to position the electrodes on, around, or in proximity to the targeted gastrointestinal tissue. The implanted leads are then subcutaneously tunneled to the pulse generator (also referred to as a controller) that is implanted in a subcutaneous pocket. The use of these lead wires is associated with significant problems such as complications due to infection, lead failure, lead migration, and electrode/lead dislodgement. Application of electrodes to the gastrointestinal tissues can be difficult, because the stomach is uniquely designed to pass material through the system; consequently, electrodes are often expelled through the system itself.

Other prior art has attempted to deal with the complications and limitations imposed by the use of electrical leads. For example, self-contained implantable microstimulators and remotely powered microstimulators implanted through the esophagus into gastrointestinal tissue have been described; however, each approach suffers from some significant limitation. A self-contained microstimulator must incorporate a battery or some other power supply; this imposes constraints on size, device lifetime, available stimulation energy, or all three.

As noted earlier, for leadless solutions in other similar stimulation applications, remotely powered devices have previously utilized either radiofrequency (RF) or electromagnetic transformer power transmission. RF energy transmission, unless the transmitting and receiving antennae are placed in close proximity, suffers from inefficiency and limited safe power transfer capabilities, limiting its usefulness in applications where recharging or stimulation must be accomplished at any significant depth (>1-2 cm) within the body, in particular where it is desired to permanently implant both the transmitter and receiver-stimulator. Electromagnetic coupling can more efficiently transfer electrical power, and can safely transfer higher levels of power (devices with capacity in excess of 20 Watts have been produced), but again relies on close proximity between transmitting and receiving coils, or the utilization of relatively large devices for deeper (5-8 cm maximum) implantation.

The methods and apparatus of the current invention utilize vibrational energy, particularly at ultrasonic frequencies, to overcome many of the limitations of currently known solutions for SCS and TENS, by achieving a spinal cord stimulation capability without the use of leads connected to a stimulation controller/pulse generator.

Nerve Stimulation

Electrical stimulation of nerves, nerve roots, and/or other nerve bundles for the purpose of treating patients has been known and actively practiced for several decades. Application of an electrical field between electrodes to stimulate nerve tissues is known to effectively modify signal pathways both with unidirectional and bidirectional stimulation along the nervous system to signal the brain or to signal organs to alleviate symptoms or control function. These applications are currently practiced with, both, externally applied devices and implanted devices. For example, applying specific electrical pulses to nerve tissue or to peripheral nerve fibers that corresponds to regions of the body afflicted with chronic pain can induce paresthesia, or a subjective sensation of numbness or tingling, or can in effect block pain transmission to the brain from the pain-afflicted regions. Many other examples include electrical stimulation of various branches of the vagus nerve bundle for control of heart rate, mediating hypertension, treating congestive heart failure, controlling movement disorders, treating obesity, treating migraine headache, and effecting the urinary, gastrointestinal, and/or other pelvic structure in order to treat urgency frequency, urinary incontinence, and/or fecal incontinence. Still other branches of the vagus nerve have been used to treat neuropsychiatric disorders. Additionally, applications are also known for electrical stimulation of nerves and nerve bundles in many other specific, selected nerve regions: for example, the pudendal or sacral nerves for controlling the lower urinary tract.

Depending on the individual patient, direct nerve stimulation can effectively modify signal pathways along the nerve, to and from the brain, and to and from organs in the body and thus provide relief of symptoms or control of bodily function. Treatment regimens and targeted nerve locations are known in related art through use of current, common stimulation devices and methods. Commonly implanted devices for nerve stimulation are made by such companies as Cyberonics, Medtronic, Advanced Bionics, and others.

The nervous system is a complex anatomical network that is organized to connect the brain to all areas of the body. The brain uses the nervous system to control bodily processes and adjust the body to its environment. The nervous system is conceptualized by two parts; the central nervous system (CNS), and the peripheral nervous system (PNS). The CNS generally consists of the brain and the spinal cord. The PNS consists of a series of nerves and nerve bundles branching out to all organs and tissue areas of the body. The PNS is connected to the CNS and thus together provides the network of control between the brain and all specific bodily functions. The central nervous system is pervasive throughout the body with individual nerves and nerve bundles reaching to all bodily functions. The PNS consists of the cervical, thoracic, lumbar, and sacral nerve trunks leading away from the spine to all regions of the body. The peripheral nervous system also includes cranial nerves. Sensory and control signals travel between the brain and other regions of the body using this network of nerves that all travel along the spinal cord.

As noted earlier, TENS is a well known medical treatment used primarily for symptomatic relief and management of chronic intractable pain and as an adjunctive treatment in the management of post surgical and post traumatic acute pain. In the context of this application, Specific Nerve Stimulation (SNS) refers to treatments for a variety of medical conditions that apply electrical stimulation directly to nerves, nerve roots, nerve bundles, tissue or regions in proximity to nerves that are in the PNS. Currently available stimulator systems for SNS are fully implanted electronic devices placed subcutaneously under the skin and connected via insulated metal lead(s) to electrodes which are invasively inserted into, around, or onto a nerve or proximate the nerve. A common implanted SNS system contains a battery to power the system. Some implanted SNS systems use an RF wireless connection instead of a battery to power the implanted device. In these RF systems, a receiver device is implanted subcutaneously and a transmitter is worn on the outside of the body. The antenna are tuned to each other and aligned such that control information and power is transmitted to the receiver and then directs the electrical impulses to the electrodes through the leads. The external transmitter contains batteries to power the transmission. All systems have the capability to externally adjust settings of the implanted system through a programming device.

In SNS and TENS systems, electrical energy is delivered through lead wires to the electrodes. For SNS, implanted electrodes are positioned on, around, or in close proximity of the nerve to be stimulated. SNS uses the implanted electrodes to deliver a variety of stimulation modalities including unidirectional and bidirectional propagation along the nerve with the electric pulse waveform defined by a plurality of variables, including, pulse width, pulse frequency (Hz) or duty cycle, amplitude (V), and waveform shape (e.g., monophasic or bi-phasic).

SNS is used for treatment of headache, migraine headache, or facial pain by selection of branches in the peripheral nervous system in the cranium or along the vagus nerve bundle. SNS is used for the treatment of chronic pelvic pain due to such conditions as lumbosacral radiculitis, lumbosacral radiculopathy, lumbosacral plexitis, lumbosacral plexopathy, vulvadynia, coccygodynia, peripheral neuritis, and peripheral neuropathy, by applying stimulation to the peripheral nervous system in the sacrum.

SNS is also applied to branches of the vagus nerve in a wide variety of applications, but not limited to the treatment of heart failure; hypertension; obesity; migraine; neuropsychiatric disorders; urinary, gastrointestinal, and/or other pelvic area structures in order to treat urinary urgency, urinary incontinence, and/or fecal incontinence. SNS is also used for severe chronic pain. Stimulation of specific nerves is known to reduce symptoms and enhance the quality of life in patients with chronic pain.

As described above, TENS and SNS devices are battery-powered electronic devices either used transcutaneously (TENS) or implanted (SNS) and connected via insulated metal lead(s) to electrodes which are either placed on the skin (TENS) over the spine or implanted onto, around, or in close proximity to the nerve or nerve bundle selected for stimulation. The implanted electrodes for SNS are positioned on leads that are placed percutaneously, through needle punctures, or through minimally invasive surgical procedures such as laminectomy, or through direct surgical access to position the electrodes on, around, or in proximity to the targeted nerve. On some leads, between 2 and 16 electrodes are available and are positioned in the region that is targeted for electrical stimulation. The implanted leads are then subcutaneously tunneled to the pulse generator (also referred to as a controller) that is implanted in a subcutaneous pocket. The use of these lead wires is associated with significant problems such as complications due to infection, lead failure, lead migration, and electrode/lead dislodgement. Application of electrodes to the nerves can be difficult because of the need to precisely locate electrodes for effective therapy.

Other prior art has attempted to deal with the complications and limitations imposed by the use of electrical leads. One such approach is using self-contained microstimulators. A self-contained microstimulator must incorporate a battery or some other power supply; this imposes constraints on size, device lifetime, available stimulation energy, or all three. Due to high use or high energy requirements of the therapeutic stimulation some SNS devices contain rechargeable batteries or are powered remotely with an RF coupling to the controller.

The methods and apparatus of the current invention utilize vibrational energy, particularly at ultrasonic frequencies, to overcome many of the limitations of currently known solutions for selected nerve stimulation, by achieving a nerve stimulation capability without the use of leads connected to a stimulation controller/pulse generator.

Brain Stimulation

Electrical stimulation of brain tissue is a growing treatment for many neurological disorders, including alleviation of Parkinson's and essential tremor diseases, chronic pain, depression, epileptic seizures, motor dysfunction due to stroke, and other emerging applications such as diabetes, obesity, and urinary control. Treatment regimens and targeted brain tissue locations are becoming known in related art through use of current, common stimulation devices and methods. Commonly implanted devices for direct brain stimulation are made by such companies as Medtronic, Cyberonics, and NeuroPace.

Deep Brain Stimulation (DBS) generally refers to treatments for a variety of medical conditions that apply electrical stimulation directly on brain tissue or in regions of the brain. Currently available stimulators for DBS are battery-powered electronic devices implanted under the skin that are connected via insulated metal lead(s) to electrodes that are inserted into or onto the brain. DBS uses the inserted electrodes to deliver a variety of stimulation modalities. For example, continuous high-frequency electrical stimulation is used in areas of the brain including the thalamus, globus pallidus (GPi), or the subthalamic nucleus (STN), or other parts of the brain to control movement disorders. High frequency stimulation of cells in these areas actually shuts them down, helping to rebalance control messages throughout the movement control centers in the brain.

DBS of the thalamus is primarily used to treat disabling tremor, especially tremor that affects one side of the body substantially more than the other. Studies have shown that DBS may significantly reduce tremor in about two thirds of patients with Parkinson's disease (PD). Tremor may not be eliminated, and may continue to cause some impairment. DBS of the globus pallidus is useful in treatment of dyskinesias as well as tremor, and may improve other symptoms, as well. DBS of the subthalamic nucleus may have an effect on most of the main motor features of PD, including bradykinesia, tremor, and rigidity.

Treatment sites for movement disorders may be identified by probing brain tissue and a site predetermined for treatment is selected. As noted for movement disorders, published regions of the brain include, but are not limited to, the ventral intermediate thalamus, subthalamic nucleus, and internal globus pallidus.

Similarly, DBS has been pursued as a treatment for pain for the past 30 years. Peripheral pain signals are transmitted via the spinothalamic tract of the spinal cord and synapse primarily in the thalamus. Thus, the area where they synapse was seen as a prime target for DBS and was the focus of much of the early research. DBS continues to be pursued as a therapy in chronic pain patients. Today, the pain indications that either exist or seem most promising for potential treatment by deep brain stimulation include: neuropathic pain; Complex Regional Pain Syndrome (CRPS), Type II; steady, burning pain; lancinating, shooting pain; tactile hypersensitivity; or partial or complete sensory loss. The targets for DBS for pain typically include the following sites:

Neuropathic Pain
Medial lemniscus
Ventrobasal (VB) area of the thalamus, including the ventral posteromedial (VPM) and the ventral posterolateral (VPL) nuclei
Internal capsule
Motor cortex
Cingulate gyrus (also known as cingulate cortex)
Posterior complex of the thalamus (PO)
Ventrolateral nucleus of the thalamus (VL)
Nociceptive Pain
Periventricular grey (PVG) matter and periaqueductal grey (PAG) matter, which are sometimes simply called periventricular grey and periaqueductal grey Similar targets in the brain are emerging for other DBS applications. Published targets for the treatment of depression would include, but are not limited to, one or more of the cerebellar vermis, the anterior cingulate gyrus, the dorsal prefrontal cortex, the dorsal raphe nuclei, the median raphe nuclei, and the locus coeruleus. Published targets for the treatment of epilepsy, obesity, and diabetes would include, but are not limited to, the nucleus of tractus solitarius (NTS), the sub thalamic nucleus, the hippocampus, the medial thalamus and the temporal lobe.

Upper regions of the brain, e.g., the cortex, that have been affected by stroke or injury also benefit from stimulation treatments and have been shown to be effective in rehabilitating motor performance of distal extremities. In this stroke rehabilitation treatment the electrode is placed on the dura, the membrane that covers the brain, and used to deliver stimulation to the cortex.

Currently available DBS devices are battery-powered electronic devices implanted under the skin connected via insulated metal lead(s) to electrodes which are inserted into the brain. The brain electrodes are placed into brain tissue via a small cranial hole and then connected to lead extensions which are subcutaneously tunneled between the skull and skin, down the back of the head, and around the neck to the battery-powered pulse generator (also referred to as a controller) that is implanted in a subcutaneous pocket in the pectoral region of the chest. Even in cases where the pulse generator may be located under, within, or on the skull the electrodes are still in direct connection to the pulse stimulator using a lead. The use of these lead wires is associated with significant problems such as complications due to infection, lead failure, and electrode/lead dislodgement.

Often, DBS devices contain rechargeable batteries due to high use or high energy requirements of the therapeutic stimulation Implantation of the pulse generator into the skull has been proposed, which addresses the difficult procedural task of tunneling leads and avoids cosmetic appearance issues associated with the subcutaneous leads and pulse generators; however, the lead still must be placed into the brain and connected to the pulse generator.

The methods and apparatus of the current invention utilize vibrational energy, particularly at ultrasonic frequencies, to overcome many of the limitations of currently known solutions for DBS, by achieving a brain stimulation capability without the use of leads connected to a stimulation controller/pulse generator.

Cochlear Stimulation

Electrical stimulation in the cochlea of the ear for the purpose of treating patients with hearing loss has been known and actively practiced for several decades. Application of an electrical field between electrodes in the cochlea stimulates cochlear nerve tissues and is known to effectively modify signal pathways to the brain to emulate the sensation of hearing sounds. These applications currently use several components including externally applied parts and implanted parts, collectively referred to as a cochlear implant system (CIS). A cochlear implant system consists of a microphone, which picks up sound from the environment; a sound-speech processor, which selects and arranges sounds picked up by the microphone; a transceiver-stimulator, which receives signals from the sound-speech processor and converts them into electric impulses; and electrodes, which collect the impulses from the transceiver-stimulator and applies them to the cochlea. As the cochlea is stimulated, signals are sent to the brain and interpreted by the brain as sound.

A CIS device does not restore or create normal hearing, nor does it amplify sound like a hearing aid. CIS provides a train of stimulation pulses that are correlated with sound and provides this interpreted pattern of impulses to the brain. The brain is capable of associating these substituted impulses as sound which enables the patient/brain to reform environmental sound recognition and speech recognition. Depending on the individual patient, cochlear stimulation can effectively activate signal pathways along the cochlear nerve, to the brain, and the brain associates these artificially induced impulses with sounds. For example, speech recognition can be accomplished in profoundly deaf patients who learn to associate these stimuli with sound, particularly in combination with reading lips. Treatment regimens and targeted cochlear nerve locations are known in related art through use of current, common stimulation devices and methods. Commonly implanted CIS devices for cochlear nerve stimulation are made by such companies as Med El Medical Electronics, Advanced Bionics, Cochlear Inc. and others.

The hearing system is an anatomical structure that begins at the ear canal. Sound travels through the canal to the ear drum which vibrates and sets in motion bones in the inner ear. This motion causes the fluid in the cochlea to move small hair cells. The hair cells transduce this movement into electrical impulses in the cochlear nerve which sends the impulses to the brain, which then interprets the impulses as sound.

CIS is a well known medical treatment used primarily to restore speech recognition in the patients with conditions that prevent the hair cells in the cochlea from activating, particularly in the profoundly deaf. Microphone, sound-speech processor, transceiver-stimulator, and electrodes are the common components for a conventional CIS device. The Microphone is typically worn behind the ear and configured for wear to hook over the top of the ear or alternatively can be worn on the clothing or placed in a pocket. There is a direct connection from the Microphone, via a wire, to the Sound-speech processor. Alternative embodiments sometimes include the Microphone and the Sound-speech processor in the same device. The Sound-speech processor interprets the sound waves it receives and converts the frequency of the sound waves into trains of pulses with varying pulse durations. The series of pulses is then sent to the Transceiver-stimulator to be converted into electrical signals to be sent between electrodes that are positioned in the cochlea. This series of pulses is communicated from the Sound-speech processor either by direct wired connection to the Transceiver-stimulator or by radiofrequency communication between the two components. The Transceiver-stimulator is implanted subcutaneously between the patient's skin and skull and the Sound-speech processor may be mounted externally on the skull proximate to the Transceiver-stimulator. The Electrodes are connected to the Transceiver-stimulator via a lead that is tunneled from the cochlea to the Transceiver-stimulator. Electrodes are dispersed along the distal end of the lead and positioned throughout the cochlea so that a variety of locations in the cochlea can be stimulated independently. Prior art describes effective processes and algorithms to convert sound into impulse trains and to send those trains to electrodes in selected cochlea regions to stimulate the cochlear nerves.

In CIS systems, electrical energy is delivered through lead wires to the electrodes. CIS implanted electrodes are positioned throughout the spiral structure of the cochlea in order to stimulate different regions in the cochlear nerve. CIS uses the implanted electrodes to deliver a variety of stimulation modalities along the cochlea and thus along the cochlear nerve with the electric pulse waveform defined by a plurality of variables, including but not limited to: pulse width or pulse frequency (Hz).

As described above, CIS devices are battery-powered electronic devices connected via insulated metal lead(s) to electrodes which are placed in the cochlea around or in close proximity to the cochlear nerve or cochlear nerve bundle. The implanted electrodes for CIS are positioned on leads that are placed percutaneously, through needle punctures or through direct surgical access to position the electrodes along the spiral shaped cochlea. A typical application may utilize 16 electrodes (for example, selected and used as 8 pairs of electrodes) positioned in regions that are targeted for electrical stimulation. The implanted leads are then subcutaneously tunneled to the Transceiver-stimulator (also referred to as a controller) that is implanted in a subcutaneous pocket between the skin and the skull. The use of these lead wires is associated with significant problems such as complications due to infection, lead failure, lead migration, and electrode/lead dislodgement. Application of electrodes to the cochlea can be difficult because of the need to locate electrodes for effective therapy. Additionally, the implanted Transceiver-stimulator must be in communication with the external Sound-speech processor. This requires that the implanted Transceiver-stimulator have a percutaneous connection to the Sound-speech processor or that an RF or magnetic coupling be maintained. A percutaneous connection is often a source for infection and wound control.

Other prior art in many stimulation applications has attempted to deal with the complications and limitations imposed by the use of electrical leads. One such attempt is the use of microstimulators. Constant communication from the Speech Processor would be required with the microstimulator imposing further constraints on maintaining a constant communication between the two devices. Due to high use or high energy requirements of the therapeutic stimulation some CIS devices contain rechargeable batteries or are powered remotely with the RF coupling to the controller.

The methods and apparatus of the current invention utilize vibrational energy, particularly at ultrasonic frequencies, to overcome many of the limitations of currently known solutions for cochlea stimulation, by achieving a cochlea stimulation capability without direct connection to the Sound-speech processor or without the use of leads connected to a controller.

Hence, it will be beneficial to have a system and method for electrical stimulation of tissue that avoids the problems associated with conventional stimulation systems. Particularly, problems due to leads. Additionally, implantable systems that can remain implanted for longer periods with minimal energy consumption would be particularly desirable.

REFERENCES

The following patents, all of which are incorporated in this disclosure in their entirety, describe various aspects of using electrical stimulation for achieving various beneficial effects. U.S. Pat. No. 4,026,304 titled "Bone Generating Method and Device" by Levy describes a stimulation protocol that uses a train of pulses rather than constant direct current or voltage, using conventional lead/electrode systems. U.S. Pat. No. 5,441,527 titled "Implantable Bone Growth Stimulator and Method of Operation" by Erickson et al. describes an implantable bone growth stimulation system with electrodes implanted in the region of bone and connected via leads to an implantable stimulator/controller. The following patents describe various methods and systems for the application of ultrasonic energy for achieving beneficial effects related to bone growth or the healing of fractures using ultrasound alone: U.S. Pat. Nos. 6,231,528 and 6,652,473 both titled "Ultrasonic and Growth Factor Bone Therapy: Apparatus and Method" by Kaufman et al., U.S. Pat. Nos. 6,322,527 and 5,556,372 titled "Apparatus for Ultrasonic Bone Treatment" by Talish, U.S. Pat. Nos. 5,752,924 and 5,547,459 titled "Ultrasonic Bone Therapy Apparatus and Method" by Kaufman et al., U.S. Pat. No. 5,496,256 titled "Ultrasonic Bone Healing Device for Dental Application" by Bock et al., U.S. Pat. No. 5,309,898 titled "Ultrasonic Bone Therapy and Assessment Apparatus and Method" by Kaufman et al., and U.S. Pat. No. 4,530,360 titled "Method for Healing Bone Fractures with Ultrasound". A publication by J D Heckman, J P Ryaby, J McCabe, J J Frey and R F Kilcoyne, "Acceleration of tibial fracture-healing by non-invasive, low-intensity pulsed ultrasound" The Journal of Bone and Joint Surgery, Vol. 76, Issue 1 26-34, 1994, describes the use of a UBGS system.

U.S. Pat. No. 3,835,833 titled "Method for Obtaining Neurophysiological Effects" by Limoge describes delivery and parameters for electrical stimulation in a TENS stimulation system. U.S. Pat. No. 4,690,144 titled "Wireless Transcutaneous Electrical Tissue Stimulator" by Rise et al. also describes delivery, systems, and application parameters for a TENS stimulation system. U.S. Pat. No. 6,735,475 titled "Fully implantable miniature neurostimulator for stimulation as a therapy for headache and/or facial pain" by Whitehurst et al. describes an implantable microstimulator used for treatment of pain in peripheral nerves generally in the skull or the cervical regions of the spine. U.S. Pat. No. 6,748,276 titled "Neuromodulation therapy system" by Daignault et al. describes an implantable SCS system that uses an external RF communication to adjust delivery of therapy. U.S. Pat. No. 6,027,456 titled "Apparatus and method for positioning spinal cord stimulation leads" by Feler et al. describes approaches to the implantation of leads into the dorsal column of a patient. U.S. Pat. No. 5,938,690 titled "Pain management system and method" by Law et al. describes methods for determining and optimizing treatment parameters and regimens for by mapping patient responses to test stimulation patterns. U.S. Pat. No. 6,002,965 titled "Epidural nerve root stimulation" by Feler et al. describes treating pelvic pain by application of stimulation in the sacral and lumbar regions of the spine.

U.S. Pat. No. 3,522,811 titled "Implantable Nerve Stimulator and Method of Use" by Schwartz et al. describes an implantable application for stimulation of the carotid sinus nerve as a treatment for hypertension. U.S. Pat. No. 6,615,081 titled "Apparatus and method for adjunct (add-on) treatment of diabetes by neuromodulation with an external stimulator" by Boveja describes an implantable application for stimulation of the vagus nerve as a treatment for diabetes. U.S. Pat. No. 6,684,105 titled "Treatment of disorders by unidirectional nerve stimulation" by Cohen et al. describes an application of electrical stimulation of nerves in unidirectional and bidirectional propagation of the electrical treatment along the nerve. U.S. Pat. No. 5,282,468 titled "Implantable neural electrode" by Klepinski describes an implantable neural electrode for stimulation in contact with nerve tissue. U.S. Pat. No. 5,330,515 titled "Treatment of pain by vagal afferent stimulation" by Rutecki et al. describes an implantable application for stimulation of the vagus nerve as a treatment for pain. U.S. Pat. No. 6,622,038 titled "Treatment of movement disorders by near-diaphragmatic nerve stimulation" by Barrett et al. describes an implantable application for stimulation of branches of the vagus nerve near the diaphragm as a treatment for movement disorders such as epileptic seizure, essential tremor, etc. U.S. Pat. No. 6,622,041 titled "Treatment of congestive heart failure and autonomic cardiovascular drive disorders" by Terry et al. describes an implantable application for stimulation of the cardiac branch of the vagus nerve as a treatment for congestive heart failure. U.S. Pat. No. 5,188,104 titled "Treatment of eating disorders by nerve stimulation" by Wernicke et al. describes an implantable application for stimulation of the vagus nerve as a treatment for eating disorders. U.S. Pat. No. 6,879,859 titled "External pulse generator for adjunct (add-on) treatment of obesity, eating disorders, neurological, neuropsychiatric, and urological disorders" by Boveja describes an external application for stimulation of the vagus nerve as a treatment for a variety of conditions for example, obesity, urological disorders, etc. where the application of the stimulation can be turned off and on by the patient or caregiver. U.S. Pat. No. 6,505,074 titled "Method and apparatus for electrical stimulation adjunct (add-on) treatment of urinary incontinence and urological disorders using an external stimulator" by Boveja describes an external application for stimulation of the sacral nerves and its branches as a treatment for a variety of urological conditions. U.S. Pat. No. 5,215,086 titled "Therapeutic treatment of migraine symptoms by stimulation" by Terry et al. describes an implantable application for stimulation of the vagus nerve as a treatment for migraine headache. U.S. Pat. No. 5,531,778 titled "Circumneural electrode assembly" by Maschino et al. describes an electrode design for attachment to a nerve. U.S. Pat. No. 5,251,634 titled "Helical nerve electrode" by Weinberg describes an electrode design for attachment to a nerve. U.S. Pat. No. 6,622,047 titled "Treatment of neuropsychiatric disorders by near-diaphragmatic nerve stimulation" by Barrett et al. describes an implantable application for stimulation of the vagus nerve as a treatment for neuropsychiatric disorders. U.S. Pat. No. 7,047,078 titled "Methods for stimulating components in, on, or near the pudendal nerve or its branches to achieve selective physiologic responses" by Boggs et al. describes an implantable application for stimulation of the pudenal nerve to control physiologic responses, for example for control of the urinary tract. U.S. Pat. No. 6,002,965 titled "Epidural nerve root stimulation" by Feler et al. describes treating pelvic pain by application of stimulation of nerves in the sacral and lumbar regions of the spine.

U.S. Pat. No. 5,716,377 titled "Method of Treating Movement Disorders by Brain Stimulation" by Rise et al. describes a typical implantable DBS system for treating movement disorders such as Parkinson's. U.S. Pat. No. 7,013,177 titled "Treatment of Pain by Brain Stimulation" by Whitehurst et al. describes an implantable DBS system that uses electrical stimulation in the form of a microstimulator in combination with drug delivery for the treatment of pain. U.S. Pat. No. 7,010,351 titled "Methods and apparatus for effectuating a lasting change in a neural-function of a patient" by Firlik et al. describes a DBS system used to treat or effectuate changes to neural function particularly by stimulation in the region of the cortex. U.S. Pat. No. 6,427,086 titled "Means and method for the intracranial placement of a neurostimulator" by Fischell et al. describes a DBS device implanted in the skull. U.S. Pat. No. 6,016,449 titled "System for treatment of neurological disorders" by Fischell et al. describes the use of a DBS device for the treatment of epilepsy. U.S. Pat. No. 5,782,798 titled "Techniques for treating eating disorders by brain stimulation and drug infusion" by Rise describes a DBS system for treating eating disorders with electrical stimulation in regions of the brain.

U.S. Pat. No. 3,751,605 titled "Method for Inducing Hearing" by Michelson describes methods for inducing the sensation of intelligible hearing by direct electrical excitation of the auditory nerve endings distributed along the basilar membrane within the cochlea. U.S. Pat. No. 4,400,590 titled "Apparatus for multichannel cochlear implant hearing aid system" by Michelson describes an intra-cochlear electrode array for electrically stimulating predetermined locations of the auditory nerve within the cochlea of the ear. U.S. Pat. No. 4,819,647 titled "Intracochlear electrode array" by Byers et al. also describes an intra-cochlear electrode array for electrically stimulating the cochlea of the ear. U.S. Pat. No. 6,671,559 titled "Transcanal, transtympanic cochlear implant system for the rehabilitation of deafness and tinnitus" by Goldsmith et al. describes an implantable application for cochlea stimulation using a system that couples communication and energy via RF or inductive coupling. U.S. Pat. No. 6,889,094 titled "Electrode array for hybrid cochlear stimulator" by Kuzma describes an implantable cochlear electrode array.

U.S. Pat. No. 4,690,144 titled "Wireless Transcutaneous Electrical Tissue Stimulator" by Rise et al. describes a transcutaneous system with electrodes attached to the skin and an external controller providing for electrical field stimulation to body tissue. U.S. Pat. No. 5,405,367 titled "Structure and Method of Manufacture of an Implantable Microstimulator" by Schulman et al. describes an implantable microstimulator used generally for stimulation of tissue. U.S. Pat. No. 6,037,704 titled "Ultrasonic Power Communication System" by Welle describes the use of ultrasound energy transfer from a transmitter to a receiver for purposes of powering a sensor or actuator without being connected by a lead/wire. U.S. Pat. No. 6,366,816 titled "Electronic Stimulation Equipment with Wireless Satellite Units" by Marchesi describes a tissue stimulation system based on a wireless radio transmission requiring the charging of a battery at the receiver and separate command signals used to control the delivery of stimulation. German patent application DE4330680A1 titled "Device for Electrical Stimulation of Cells within a Living Human or Animal" by Zwicker describes a general approach to power transfer using acoustic energy for tissue stimulation.

Many designs have been disclosed to eliminate leads in stimulation systems or to develop systems that are locally implanted with integrated electrodes. For example, the following patents describe various stimulator designs: U.S. Pat. No. 3,943,936 to Rasor describes a stimulator where a self-powered, self-contained pacer and stimulator implanted in the body and the system takes advantage of the body's movement to derive the energy needed for stimulation; U.S. Pat. No. 3,486,506 to Auphan describes a spring driven cardiac stimulator where the motion of the heart is captured in a balance wheel, which in turns oscillates a permanent magnet motor that induces electric pulses that could be applied to stimulate the heart; U.S. Pat. No. 5,193,540 to Schulman discloses an implantable microstimulator that could be expelled from a hypodermic needle and derives energy by RF induction; U.S. Pat. No. 5,358,514 to Schulman describes an implantable micro-miniature stimulator and/or sensor with self-attaching electrodes; U.S. Pat. No. 5,405,367 to Schulman describes a structure and method of manufacture of an implantable microstimulator that is described in U.S. Pat. No. 5,358,514; U.S. Pat. No. 5,411,535 to Fujii describes a cardiac pacemaker using wireless transmission; U.S. Pat. No. 5,814,089 to Stokes discloses a leadless multisite implantable stimulus and diagnostic system that uses high frequency signals comprising a power component derived from a power source and using this power to stimulate tissue; U.S. Pat. No. 6,141,588 to Cox describes an implantable stimulation system with multiple stimulators where the stimulators are described as satellites in wireless communication with a "planet" control unit and receive instructions and electric power wirelessly; U.S. Pat. No. 6,654,638 to Sweeney discloses an implantable electrode that can be activated by ultrasound; U.S. Pat. No. 7,003,350 to Denker describes intravenous cardiac pacing system with wireless power supply based on RF signals; and U.S. patent application Ser. No. 10/632,265 to Penner discloses an implantable electrode that can be activated by ultrasound.

BRIEF SUMMARY OF THE INVENTION

This invention relates to methods and devices for using electrical stimulation to achieve salutary effects in tissue. The invention is a system comprising a controller-transmitter that transmits vibrational energy and signal information, an implanted receiver-stimulator that is capable of receiving the transmitted vibrational energy and converting it into electrical energy, and stimulation electrodes, such that the stimulation electrodes would be in contact with the desired tissue, in close proximity to the tissue, and apply the electrical energy to the tissue.

In one embodiment, the controller-transmitter could be implanted. In another embodiment, the controller-transmitter could be located on the external surface of the body. When located externally, the controller-transmitter could be attached to a strap, belt, or harness. The transmitted vibrational energy would be directed to the receiver-stimulator to cause electrical stimulation at the electrodes of the receiver-stimulator to achieve the desired biological or therapeutic effect. Transmission of vibrational energy and application of electrical stimulation could be applied continuously, or temporarily at prescribed intervals when periodic stimulation is sufficient.

The tissue to be treated could be bone, spine, specific nerves, the gastrointentinal tract, brain or cochlea.

For beneficial effects of stimulation on bone, this application of leadless electrical stimulation is for accelerating bone healing by stimulation. Bone healing includes bone fractures, bone fusions, or joint replacement that may also involve the surgical attachment of associated devices, e.g., pins, cages, plates, or bone grafts. The invention is a system comprising a controller-transmitter, an implanted receiver-stimulator, and stimulation electrodes, such that the stimulation electrodes would be in contact with bone, in close proximity to the bone, or in contact or proximity to devices used to facilitate the bone fusion/repair. In other embodiments, the receiver-stimulator would be directly incorporated into the associated device, e.g., pin, cage, plate, graft material/process, or prosthetic joint with electrodes placed as appropriate to stimulate the bone in a desired location or locations.

In another embodiment for bone healing, the system is adapted to simultaneously provide ultrasonic bone treatment with electrical stimulation. In such a system, the vibrational energy from the controller-transmitter is delivered at ultrasonic frequencies with other characteristics such as are known to enhance bone growth and promote healing. Such a controller-transmitter is either implanted or externally applied. The implanted receiver-stimulator, as previously described, is adapted to intercept at least a portion of the applied ultrasonic energy and convert it to electrical energy for direct electrical stimulation of the desired site. Such a combination of ultrasonic and electrical bone growth stimulation provides enhanced therapy relative to either technique alone.

Another application of leadless electrical stimulation is for spinal cord stimulation purposes, where the stimulation acts on the nerves to reduce pain. The invention is a system comprising a controller-transmitter, an implanted receiver-stimulator, a programmer to adjust therapy parameters, and stimulation electrodes, such that the stimulation electrodes would be in contact with tissue in the spine regions, in close proximity to the tissue or region to be stimulated to facilitate treatment.

In one use of the external embodiment of the controller-transmitter, the device is for pain management of recurring but not continuous pain, for example, headache pain. In the external embodiment, miniaturized receiver-stimulator devices are implanted, but the controller-transmitter unit is external to the body, possibly hand-held or worn attached to a belt or harness. The acoustic energy from the external controller-transmitter is coupled through the skin as well as any underlying tissues, to the implanted device. The external controller-transmitter is under control of the patient. Thus, when the patient begins to feel pain, the controller-transmitter unit is applied and/or switched on, and certain characteristics, for example, the level of stimulating energy and possibly the frequency or pulse duration of the stimulating waveform, is modified by the user, enabling the user to tailor the stimulation as needed to diminish the pain.

Another application of leadless electrical stimulation is for specific gastrointestinal tissue applications. The invention is a system comprising a controller-transmitter, an implanted receiver-stimulator, a programmer to adjust therapy parameters, and stimulation electrodes, such that the stimulation electrodes would be in contact with gastrointestinal tissue or in close proximity to the gastrointestinal tissue to be stimulated to facilitate treatment.

In one use of the external embodiment of the controller-transmitter, the device is for fecal incontinence, in another use the external embodiment is for treating obesity. In the external embodiment, miniaturized receiver-stimulator devices are implanted, but the controller-transmitter unit is external to the body, possibly hand-held or worn attached to a belt or harness. The acoustic energy from the external controller-transmitter is coupled through the skin as well as any underlying gastrointestinal tissues, to the implanted device. The external controller-transmitter is under control of the patient. Thus, for examples, when the patient begins to feel discomfort, or the patients feels hungry, the controller-transmitter unit is applied and/or switched on, and certain characteristics, for example, the level of stimulating energy and possibly the frequency or pulse duration of the stimulating waveform, is modified by the user, enabling the user to tailor the stimulation as needed.

Yet another application of leadless electrical stimulation is for specific nerve stimulation applications where the stimulation acts unidirectionally or bidirectionally between the peripheral nerve and the brain. The invention is a system comprising a controller-transmitter, an implanted receiver-stimulator, a programmer to adjust therapy parameters, and stimulation electrodes, such that the stimulation electrodes would be in contact with nerves, in close proximity to the nerve or nerve tissue region to be stimulated to facilitate treatment.

In one use of the external embodiment of the controller-transmitter, the device is for treating urge incontinence; in another use of the external embodiment, it is for recurring but non-continuous pain, for example, headache.

Another application of leadless electrical stimulation is for deep brain stimulation, where the stimulation acts on the brain to reduce symptoms or effectuate change in the neural response of the brain. The invention is a system comprising a controller-transmitter, an implanted receiver-stimulator, and stimulation electrodes, such that the stimulation electrodes would be in contact with brain tissue, in close proximity to the tissue or brain region to be stimulated to facilitate treatment.

In one embodiment, the controller-transmitter could be implanted. The controller-transmitted could be implanted between the skull and the skin or it could be adapted to be implanted under the skull or yet it could be adapted to be implanted in a section of skull that has been removed. In another embodiment, the controller-transmitter could be applied on the external surface of the head. The transmitted vibrational energy would be directed to the receiver-stimulator to cause electrical stimulation at the electrodes of the receiver-stimulator.

An example of use for an external use of the controller-transmitter is for pain management of chronic recurring but not continuous pain. Miniaturized receiver-stimulator devices are implanted, but the controller-transmitter unit is external to the brain, possibly hand-held or worn attached to a belt or harness. The acoustic energy from the external controller-transmitter is coupled through the skin as well as any underlying tissues, to the implanted device. The external controller-transmitter is under control of the patient. Thus, when the patient begins to feel discomfort, the controller-transmitter unit is applied and/or switched on, and certain characteristics, for example the level of stimulating energy and possibly the frequency or pulse duration of the stimulating waveform, is modified by the user, enabling the user to tailor the stimulation as needed to diminish the pain. Similar utility under patient control would be useful for tremor or seizure and the like.

Another aspect of this invention relates to methods and devices for using electrical stimulation in the cochlea of the ear as a treatment for hearing loss, effectively modifying signal pathways along the cochlear nerve, to the brain, to provide a functional capability of hearing, particularly for environmental sound recognition and speech recognition.

This application of electrical stimulation is to specifically eliminate one or more direct lead connections between the components of a Cochlear Implant System. The invention is a system comprising a microphone, a sound-speech processor, a controller-transmitter, and an implanted receiver-stimulator with stimulation electrodes, such that the stimulation electrodes would be implanted in the cochlea of the ear, in close proximity to the cochlear nerve or cochlear nerve bundle to be stimulated to facilitate a sensation of sound in the brain.

In one preferred embodiment, the receiver-stimulator is implanted such that electrodes of the receiver-stimulator are within the cochlea of the ear. In one embodiment of the receiver-stimulator, the receiver-stimulator is positioned at one implantation site and connected to the electrodes in the cochlea via a lead. In another embodiment of the receiver-stimulator, the receiver-stimulator is adapted to be implanted within the cochlea and multiple electrodes are dispersed on the device throughout the cochlea. In yet another embodiment of the receiver-stimulator, the receiver-stimulator is miniaturized to contain a pair of electrodes and multiple receiver-stimulator devices are individually positioned within the cochlea. The transmitted vibrational energy is directed to the receiver-stimulator to cause electrical stimulation at the electrodes of the receiver-stimulator.

In the implanted embodiment of the controller-transmitter, the sound-speech processor communicates with the controller-transmitter via RF, electromagnetic or acoustic coupling. In the external embodiment of the controller-transmitter, the controller-transmitter may be directly connected to the sound-speech processor or be incorporated with the sound-speech processor into a single device. The acoustic energy from the external controller-transmitter is coupled through the skin as well as any underlying tissues, to the implanted receiver-stimulator device. The external controller-transmitter is under control of the sound-speech processor. Thus, when the microphone picks up sound, the sound-speech processor converts the sound into associated stimulation characteristics, for example the frequency or pulse duration of the stimulating waveform or selected electrodes in specific regions within the cochlea, the stimulation characteristics are communicated to the controller-transmitter and vibrational energy is transmitted to the receiver-stimulators. This process enables the system to convert sound into stimulation impulses in the cochlea without direct connections the electrodes.

Systems incorporating the concepts presented have advantages over currently available devices, particularly by eliminating the requirement for electrical leads, and by providing the capability for simultaneous or sequenced stimulation of multiple sites.

BRIEF DESCRIPTION OF THE DRAWINGS

The invention has other advantages and features which will be more readily apparent from the following detailed description of the invention and the appended claims, when taken in conjunction with the accompanying drawings, in which:

FIG. 4a is a schematic showing the leadless bone stimulation system in application at a tibial fracture site.

FIGS. 15a and 15b are block diagrams showing the components of the acoustic transmitter-controller and acoustic receiver-stimulators of the present invention.

DETAILED DESCRIPTION OF THE INVENTION

The systems and devices described here comprise a controller-transmitter device that will deliver vibrational energy and signal information to one or more implanted receiver-stimulator device(s) that will convert the vibrational energy to electrical energy of a form that can be used to electrically stimulate tissue. The vibrational energy can be applied with ultrasound as a single burst or as multiple bursts or as a continuous wave with appropriate selection of the following parameters:

| Parameter | Value Range |
|---|---|
| Ultrasound frequency | 20 kHz-10 MHz |
| Burst Length (#cycles) | 3-Continuous |
| Stimulation Pulse Duration | 0.1 μsec-Continuous |
| Duty Cycle | 0-100% |
| Mechanical Index | ≤1.9 |

The controller-transmitter device contains an ultrasound transducer or transducers of appropriate size(s) and aperture(s) to generate sufficient acoustic power to achieve the desired stimulation at the location of an implanted receiver-stimulator device. Additionally, multiple implanted receiver-stimulator devices may be placed within the region insonified by the controller-transmitter device. Multiple receiver-stimulator implants may function simultaneously; it is also possible for multiple devices to function independently, either by responding only to a specific transmitted frequency, or through the use of a selective modulation technique such as pulse width modulation, or through encoding techniques such as time-division multiplexing.

In the implanted version, the controller-transmitter device containing the transmitting transducer is implanted typically just beneath the skin in the subcutaneous space. In the non-implanted version, the transducer portion is placed over the skin near the targeted bone and acoustic gel or other means is placed between the transducer face and the skin surface to ensure adequate acoustic coupling.

Figure 1:
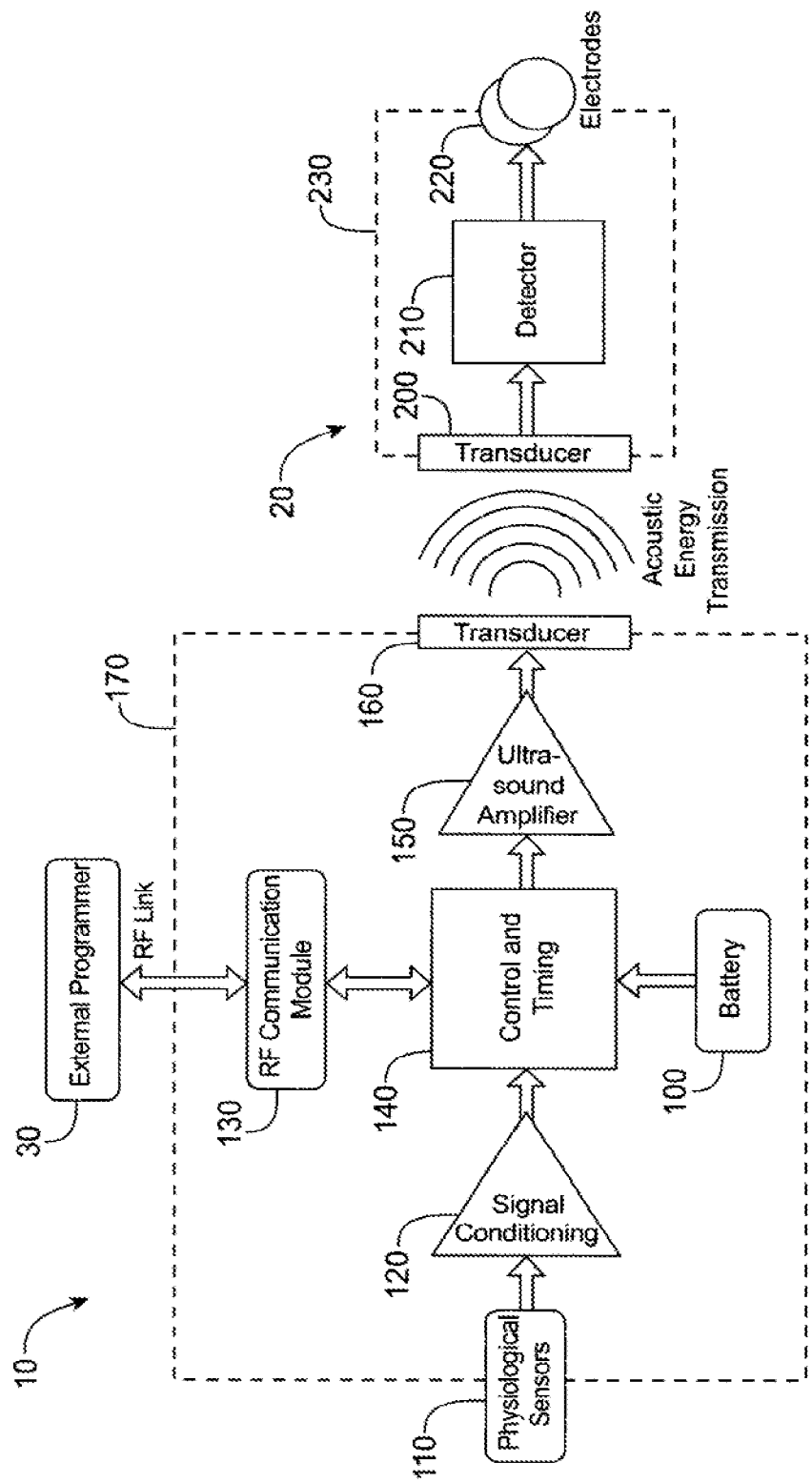
FIG. 1 shows the leadless tissue stimulation system.

FIG. 1 shows details of the system described above. In FIG. 1, the controller-transmitter unit 10 comprises: a battery 100, one or more sensors 110, signal processing circuitry 120, a communications module 130, a control and timing module 140, an ultrasound amplifier 150, and an ultrasound transducer 160. Ultrasound transducer unit 160 can also be an array of ultrasound transducers. The battery 100 which provides power for the controller-transmitter may be of a type commonly used in implanted medical devices such as a lithium iodine cell or lithium silver vanadium oxide cell made by Greatbatch, Inc. or which is optionally a rechargeable battery. One or more sensors 110 are used to detect physiological parameters. Suitable sensors are known for the detection of electrical activity, temperature, motion, pressure, and the like. These sensors are connected to signal processing circuitry 120 and optionally used by the circuitry to adjust delivery of stimulation therapy or to communicate diagnostic information from the sensors. The communications module 130 provides a data path to allow the physician to set device parameters and to acquire diagnostic information about the patient and/or the device. The data path may be by an RF communication link, magnetic coupling, ultrasound pulses, or the like, and would communicate to and from an external unit 30. Device parameters would be used by the control and timing module 140. Device parameters would include adjustments to transmissions, such as power amplitude, pulse duration, duty cycle, and the like. The control and timing module 140 uses device parameters in conjunction with the acquired physiological data to generate the required control signals for the ultrasound amplifier 150, which in turn applies electrical energy to the ultrasound transducer 160, which in turn produces the desired acoustic beam. The controller-transmitter device 10 is encased in a hermetically sealed case 170 constructed of a bio-compatible material, similar to current SCS devices.

Referring to FIG. 1, the receiver-stimulator device 20, implanted in the path of the acoustic beam at the location where electrical stimulation is desired, contains an ultrasound transducer 200, an electrical circuit 210, and electrodes 220. Ultrasound transducer 200, typically made of a piezoelectric ceramic material, a piezoelectric single crystal, or piezoelectric polymer or copolymer films, intercepts a portion of the transmitted acoustic energy and converts it into an electrical current waveform from the original alternating nature of the applied ultrasound pressure wave. Ultrasound transducer unit 200 can also be an array of transducers. This electrical signal is applied to an electrical circuit 210 which may be one of a type commonly known as an envelope detector, and which may have one of many known circuit configurations; for example, a full-wave rectifier, a half-wave rectifier, a voltage doubler or the like. Electrical circuit 210 produces a voltage pulse with amplitude proportional to the amplitude of the transmitted ultrasound burst and with a pulse length generally equal to the length of the transmitted burst. The circuit 210 may also have different configurations and functionalities, and provide output signals having characteristics other than a pulse. This signal is then applied to electrodes 220, which are typically made of platinum, platinum-iridium, gold, or the like. These may be incorporated onto the outer surface of the device, and thus in direct contact within the epidural layer or within close proximity of nerves or nerve fibers which are to be treated by stimulation. Alternatively, the electrodes 220 are connected via wires to a main body that consists of the transducer 200 and electrical circuit 210 and the electrodes 220 are adapted to be shapeable, malleable configurations that can conform to the tissue that needs to be stimulated. Electrodes may be adapted that are round, long, segmented, etc. to increase surface area or to control current density at the electrode. Electrodes may be placed on opposing sides of the tissues or in linear alignment with the tissue or in any arrangement suitable for the size and location of the spine and the targeted spine stimulation site. The receiver-stimulator device 20 is also enclosed within a sealed case 230 of biologically compatible material.

Figure 2:
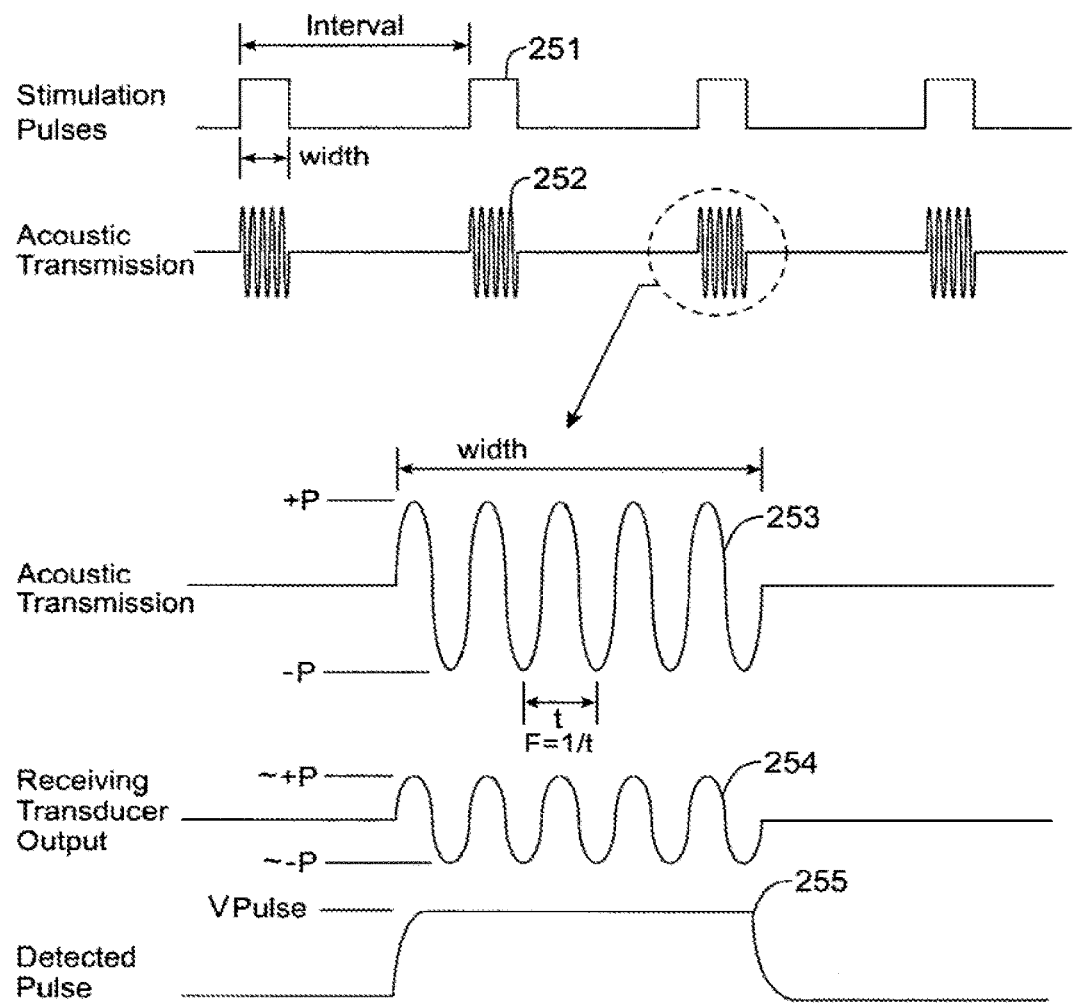
FIG. 2 illustrates representative acoustic and electrical signals useful in the systems and methods of the present invention.

Referring also to previously described FIG. 1, FIG. 2 provides detail representing exemplary acoustic and electrical signals of the present system. FIG. 2 first depicts a train of electrical stimulation pulses 251 which have a desired width and are repeated at a desired interval. The controller-transmitter device 10 produces acoustic transmissions 252, for the desired stimulation pulse width and repeated at the desired stimulation pulse interval, which are emitted from the ultrasound transducer 160. Below the waveform 252 is shown an enlargement 253 of a single acoustic burst. This burst again has a desired width, a desired oscillation frequency F=1/t, and also a desired acoustic pressure indicated by the peak positive pressure P+ and peak negative pressure P−. The acoustic pressure wave, when striking the receiving transducer 200 of the receiver-stimulator device 20 generates an electrical signal 254 having frequency and burst length matching that of the transmitted waveform 33 and amplitude proportional to the transmitted acoustic pressure (~+/−P). This electrical waveform is then rectified and filtered by the circuit 210 producing the desired pulse 255 with length equal to the burst length of the transmitted waveform 253 and amplitude (VPULSE) proportional to the amplitude of the electrical signal 254. Thus, it can be seen that it is possible in this example to vary the stimulation rate by varying the time between ultrasound bursts, to vary the duration of any one stimulation pulse by varying the duration of the ultrasound burst, and to vary the amplitude of the stimulation pulse by varying the amplitude of the transmitted ultrasound waveform. Circuit 210 could be configured to produce a direct current (DC) output or an alternating current (AC) output, or an output with any arbitrary waveform. Varying the use of signal information within the ultrasound transmission for pulse duration, pulse amplitude, and duty cycle would result in any type of burst sequencing or continuous delivery waveform effective for brain stimulation. Using signal information in the ultrasound transmission the resultant waveshape may be a square wave, triangle wave, biphasic wave, multi-phase wave, or the like.

In practice, the amount of acoustic energy received by the implanted receiver-stimulator device will vary with ultrasound attenuation caused by loss in the intervening tissue, with spatial location of the receiver-stimulator device with respect to the transmitted ultrasound beam, as such a beam is typically non-uniform from edge-to-edge, and possibly with orientation (rotation) of the receiver-stimulator device with respect to the first. Such variation would affect the amplitude of the stimulating pulse for a given ultrasound transmit power (acoustic pressure amplitude). This limitation can be overcome by adjusting the ultrasound transmit power until the resultant stimulation waveform is consistent, a technique similar to that used currently to determine stimulation thresholds at the time of cardiac pacemaker implantation. Another approach would be to automatically adjust using sensing and logic within the first device. The first device would periodically sense the electrical output of the receiver-stimulator device and adjust power transmission accordingly to compensate for any change in the system including relative movement between the transmitting and receiving devices. Yet another embodiment for overcoming this limitation is where the transducer incorporated into the receiver-stimulator device is omni-directional in its reception capability. For example, to improve omni-directional sensitivity, the transducer may be spherical in shape or have specific dimensional characteristics relative to the wavelength of the transmitted ultrasound. Alternatively, multiple transducers are disposed at appropriate angles to reduce or eliminate the directional sensitivity of the device.

Figure 3A:
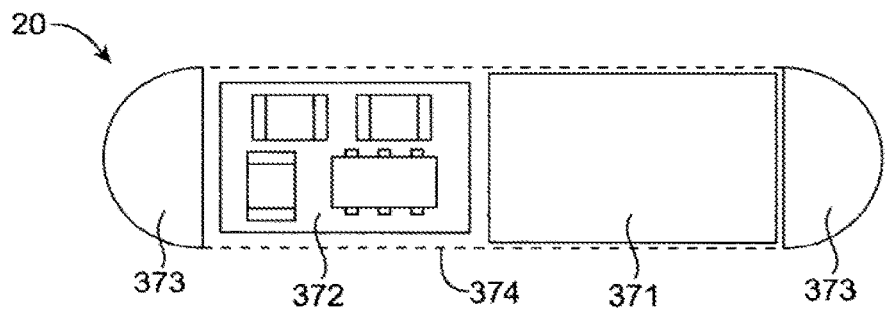
FIGS. 3a-3c are schematic illustrations showing components of the present invention.
Figure 3B:
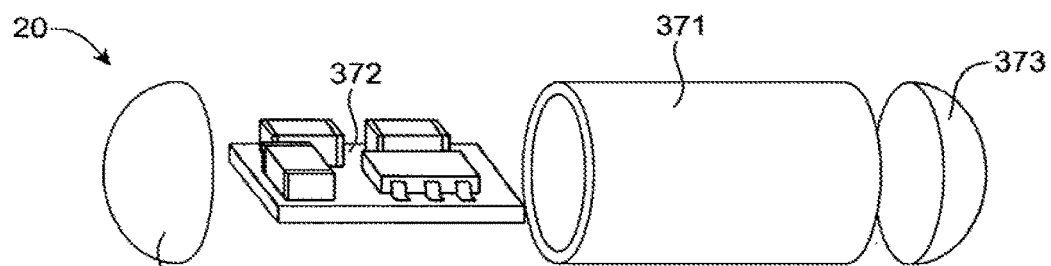
Figure 3C:
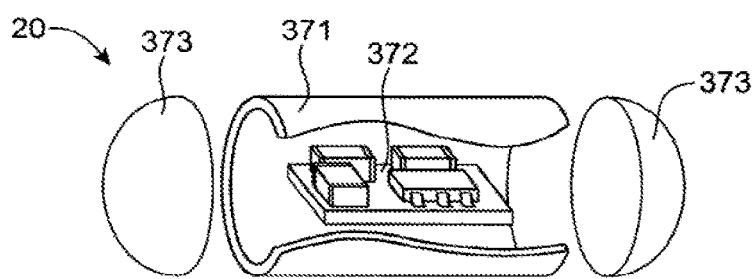

FIGS. 3a through 3c illustrate two embodiments of a small implantable receiver-stimulator of a cylindrical profile, suitable perhaps for placement by stylet or by injection through a hypodermic needle. FIG. 3a shows in plan view and 3b in perspective view such a receiver-stimulator 20 having a hollow, cylindrical ultrasound transducer 371, a circuit assembly 372 comprising the detector, and two electrodes 373 at either end of the assembly. It can be appreciated that any number of electrodes may be adapted to this embodiment. The transducer 371 would be made of an appropriate piezoelectric ceramic material, having two electrical activity contacts deposited on the outer and inner surfaces of the cylinder, respectively. The transducer and circuit would be encapsulated in an electrically insulating but acoustically transparent medium 374. The transducer 371 would be of a rigid piezoelectric material, typically a piezo-ceramic with electrodes deposited on the outer and inner surfaces of the cylinder. The circuit assembly 372 may be fabricated using known surface-mount or hybrid assembly techniques, upon either a fiberglass or ceramic substrate. Stimulation electrodes 373 would be fabricated of material commonly used in implanted electrodes, such as platinum, platinum-iridium, or the like. Necessary electrical wiring between the transducer, circuit board, and electrodes is not shown in these drawings. Typical dimensions of such a device would be 1.5 cm in length and 1.5 mm in diameter, and preferably smaller. Multiple electrodes could be adapted as appendages to the embodiment (not shown) or incorporated into fixation elements such as helical screws or barbs (not shown).

As shown in FIG. 3c, by using hybrid circuit techniques it may be possible to further miniaturize the circuit assembly 372 such that it would fit inside the hollow interior of the transducer 371. This would have the benefit of substantially reducing the length of the finished device.

While the tissue stimulation systems have been described in general terms, it should be appreciated that the systems described above can be adapted to stimulate specific tissues such as the bone, the spine, etc. Various embodiments adapted to serve such specific purpose are described in the examples below.

EXAMPLES

Example 1: Bone Stimulation

In FIG. 4a, a controller-transmitter device 10 containing circuitry to provide stimulation control and ultrasound transmission, plus means to communicate with an outside programmer 30 is implanted just beneath the skin, and generally oriented such that the transmission is over the targeted bone fracture site. An ultrasound signal is transmitted by this device 10 through intervening tissue to the receiver-stimulator device 20 containing means to receive this acoustic energy and convert it into an electrical current which may then be applied to the attached electrodes. Alternatively, the ultrasound transmission is configured such that the targeted bone fracture site receives sufficient ultrasonic energy to promote bone healing, in addition to providing the receiver-stimulator device with sufficient energy to provide electrical stimulation. In FIG. 4a, this receiver-stimulator device 20 is shown attached to a section of bone in a tibial fracture. However, it should be noted that the receiver-stimulator 20 could also be attached to any bone or site near any bone that is the target of treatment. The receiver-stimulator device 20 is shown here as a small button-shaped device that would be affixed to the bone. Other appropriate shapes could be cylindrical, hexagonal, oblong, etc. Alternatively, the functional components of the receiver-stimulator may also be separated. In one embodiment (not shown) the electrodes are applied directly to the bone or to tissue near the bone and connected by small wires to the receiver. This embodiment would adapt the electrode to be shapeable, malleable configurations that conform to the bone as flexible wraps, cages, bindings, etc. or that could be placed near the bone. Electrodes may be adapted that are round, long, segmented, etc. to increase surface area or to control current density at the electrode. Electrodes may be placed on opposing sides of the bone in linear alignment with the bone or in any arrangement suitable for the size and location of the bone and the targeted bone healing site.

Figure 4B:
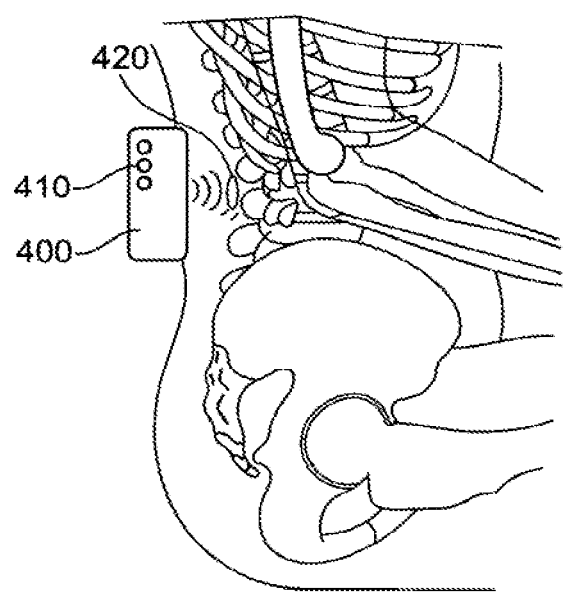
FIG. 4b is a schematic showing the leadless bone stimulation system applied at the spine.

Another embodiment of the system is illustrated in FIG. 4b. In an application of an electro-acoustic stimulation system for the treatment of spinal fusion, a receiver-stimulator device 20 is shown implanted near the spinal column, with electrodes placed so as to provide electrical stimulation to a specific region of the spine. An external acoustic controller-transmitter device 400 is placed over the area of the implant to activate the stimulation. The external transmitter 400 may be handheld, or worn on the body, attached by a belt, harness, or the like. Controls 410 may be provided to allow the user to adjust ultrasound parameters. Such ultrasound parameters, possibly including amplitude, pulse duration, and pulse repetition frequency, are selected to effect fusion of the bone or bone graft. The external controller-transmitter 400 would comprise an adjustable pulse/frequency generator, ultrasound amplifier, ultrasound transmitter, and battery. Optionally, the battery may be a rechargeable type.

In another embodiment of this invention, the controller-transmitter unit shown in FIG. 4*b* could be implanted to enable long-term continuous treatment to the spine.

Figure 5A:
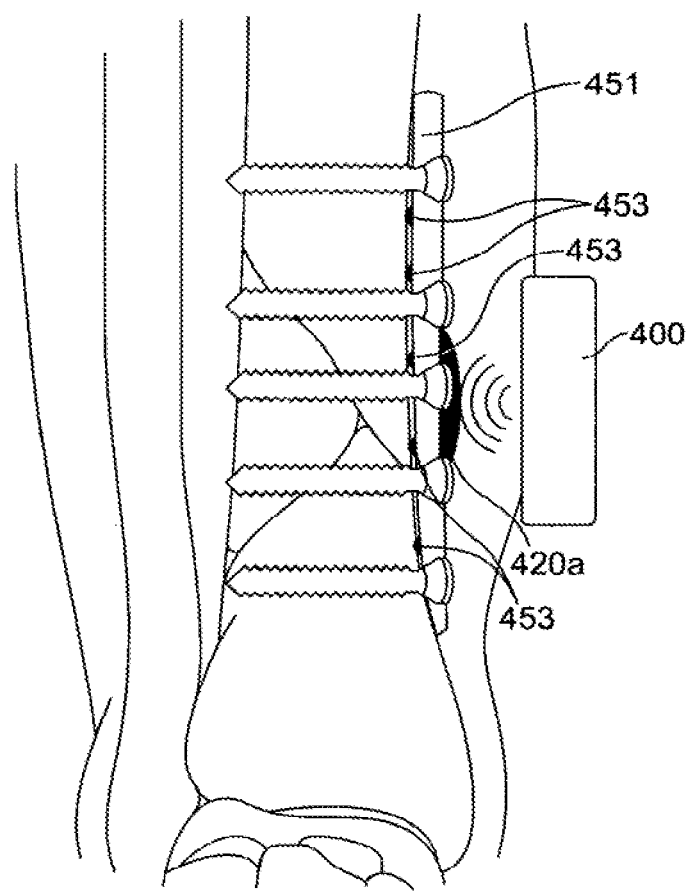
FIGS. 5a, 5b, and 5c are schematic illustrations showing components of the present invention adapted for use with devices commonly used for connecting bone fractures.
Figure 5B:
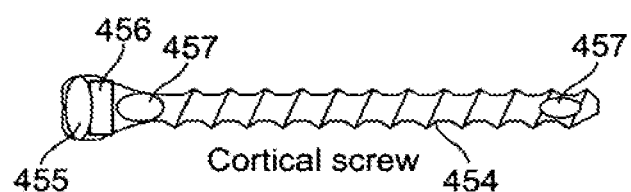
Figure 5C:
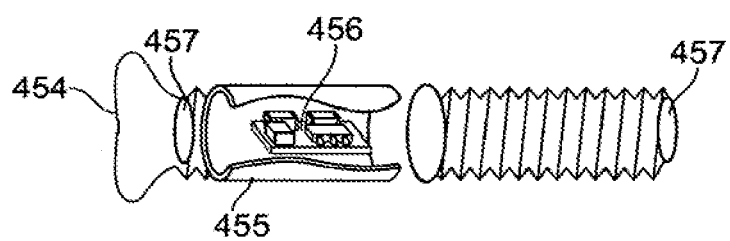

In a different embodiment of this invention, the implanted receiver and stimulation components are incorporated into an associated implanted device. For example, the receiver and stimulation components can be part of a pin, a rod, a cage, or plate used to stabilize a fracture. In such a combined device, the receiver-stimulator is adapted into the form of the associated device to provide the electrical stimulation to facilitate fusion. Referring to FIG. 5*a*, a metal plate 451 is attached with screws in a typical application to stabilize a severely fractured tibia. In this case the receiving transducer and detector electronics 420*a* and multiple electrodes 453 are incorporated onto the metal plate, with the electrodes in contact with the bone. An external controller-transmitter device 400 similar to that described above is placed over the implanted plate and held in place with a strap or harness and energized as prescribed. Alternatively the controller-transmitter can be of the type that is fully implanted. Additional applications of such a system are, for example, the incorporation of the receiver-stimulator device into the structure of a prosthetic joint or patched in place while applying bone graft materials. Referring to FIGS. 5*b* and 5*c*, a cortical screw 454 is adapted to be a receiver-stimulator including the receiving ultrasound transducer 455, circuitry 456 and electrodes 457. Similarly other associated devices for bone fusion may be adapted to contain the receiving, circuitry, and electrode elements and be used as the receiver-stimulator in the system.

Though the uses and configurations differ among the above described example bone stimulation devices, all share the same basic components of a transmitting device and one or more implanted receiver-stimulator devices. The transmitting device, whether in implantable or externally-applied embodiments, and the typical functions that may be incorporated into the transmitting device, have been described. The receiver-stimulator device, in particular with respect to the receiving ultrasound transducer, will have characteristics that are optimized for certain applications.

Figure 6A:
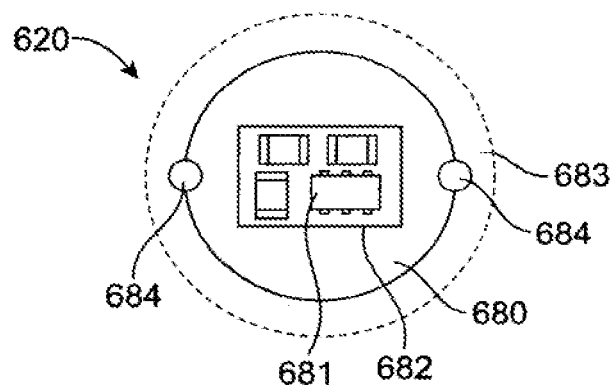
FIGS. 6a through 6c depict various embodiments for an implantable receiver-stimulator utilizing a planar transducer.
Figure 6B:
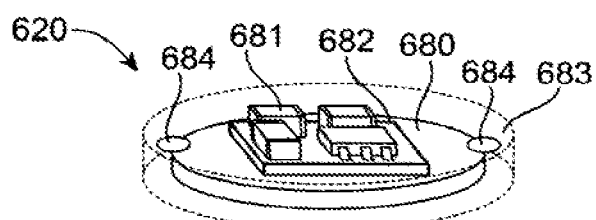
Figure 6C:
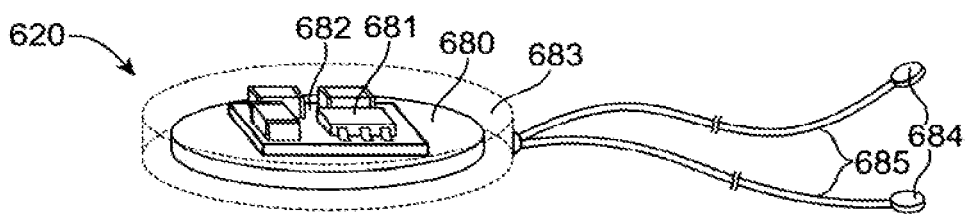

FIGS. 6*a* through 6*c* depict various possibilities for an implantable receiver-stimulator using a planar transducer. Such an embodiment may, for example, be suitable for surgical implantation for stimulation of bone or may be suitable for incorporation into associated devices such as orthopedic plates or prostheses. FIGS. 6*a* and 6*b* show in plan and perspective views, respectively, a receiver-stimulator device 620 having a circular planar ultrasound transducer 680, made typically of a piezoelectric ceramic or single crystal material having electrical contacts deposited on the top and bottom planar surfaces. The size of the ultrasound transducer 680 is selected, for example to be less than one-half wavelength, to optimize receiver sensitivity with respect to orientation. On one surface of the transducer is mounted a circuit assembly 682 containing circuit components 681, the transducer being electrically connected to the circuit components by wiring (not shown). To control any acoustic effects due to combining the components in the receiver-stimulator, the design for mounting of the circuit assembly 682 with the transducer is appropriately chosen; for example, use of air gaps or equivalent. The output of the circuit is connected to two or more stimulation electrodes 684 which are mounted on the outside of an acoustically transmissive and biocompatible casing 683 which also hermetically seals the transducer and circuitry. Electrodes 684 may be positioned on any surface or surfaces of case 683. The planar transducer 680 and case 683 may be circular as shown, or any other shape that may be suitable to the application or intended implant location.

In FIG. 6*c*, a receiver-stimulator 620 similar to that of FIGS. 6*a* through 6*b* is shown, though electrodes 684 are now shown disposed remotely from the case 683, located at the ends of flexible cables 685. Such an embodiment would facilitate precise placement of the stimulating electrodes, perhaps in a situation where it would be otherwise inconvenient or impossible to locate a device having integrated electrodes, as on opposing sides of a bone fracture.

An additional potential benefit of the bone-healing stimulator lies in the reported beneficial aspects of ultrasound exposure alone in accelerating the healing of both bone and soft tissue (bone/ligament/tendon) injuries. In all these devices, combined electrical and ultrasound stimulation would be delivered, providing an enhanced treatment compared to either electrical or ultrasound stimulation alone.

In another embodiment of this invention, the implanted bone stimulation electrodes could be used to deliver therapeutic agents. It is well established that an electric field or ultrasonic field could be beneficially used to enhance the transport of molecules through biological tissue (e.g., iontophoresis, electroporation, or sonophoresis). In one embodiment of this invention, the stimulating electrodes could be coated with a sustained release formulation of a beneficial agent. In another embodiment a reservoir containing a beneficial agent could be attached to the stimulating electrodes. Each time the electrodes are activated the beneficial agent could be released. In yet another embodiment the acoustic energy itself acts as a trigger to release beneficial agent that is contained in a reservoir or in a membrane or the like that is a component of the receiver-stimulator. The beneficial agent could be a bone growth factor, bone cement, stem cells that promote bone healing and growth and the like.

Example 2: Spine Stimulation

Figure 7:
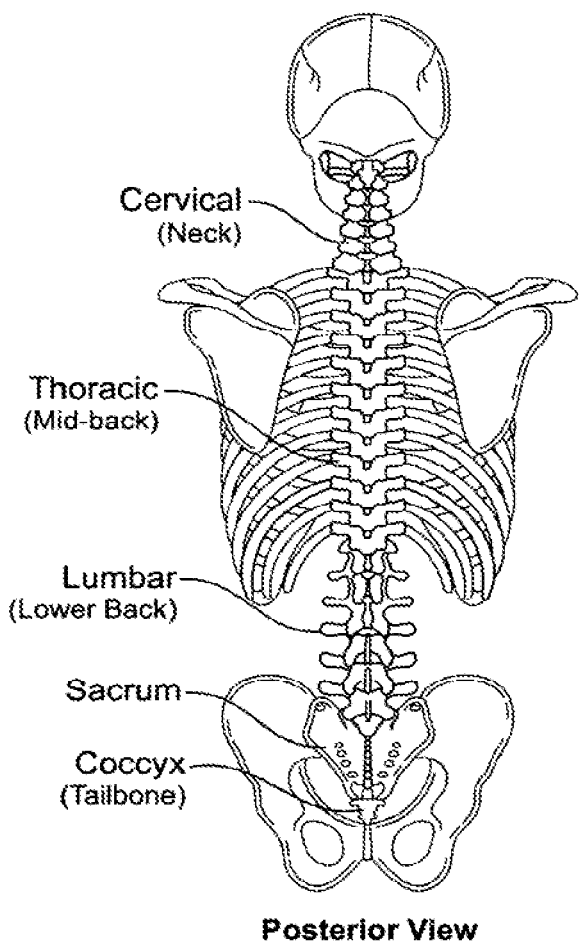
FIG. 7 is a schematic showing the basics of the spinal cord anatomy.

As described in the Background section, the spine is an anatomical structure that consists of bones (vertebrae), cartilage (discs), and the spinal cord (a nervous system structure that generally bundles or collects various nerves connecting peripheral areas of the body to the brain). As illustrated in FIG. 7 the spine is divided into five regions: (i) cervical (neck), (ii) thoracic (mid-back), (iii) lumbar (lower back), (iv) sacrum, and (v) coccyx (tailbone). The peripheral nervous system refers to the cervical, thoracic, lumbar, and sacral nerve trunks leading away from the spine to all regions of the body. The peripheral nervous system also includes cranial nerves. Pain signals travel between the brain and to other regions of the body using this network of nerves that all travel along the spine as part of the spinal cord.

A leadless pulse stimulator would be applied as follows. Using a percutaneous needle delivery technique that is used to access the epidural space, a miniaturized receiver-stimulator device disposed within the delivery needle is implanted into tissue or attached to the desired location in the epidural space. Various techniques and tools for spinal access and probing of nerve tissue are commonly known. These could be adapted to facilitate delivery of the receiver-stimulator to these locations; the receiver-transmitter may incorporate means to provide permanent attachment to the implant site including possibly helical coils, barbs, tines, or the like. Alternatively, the receiver-stimulator could be implanted during a minimally invasive surgical procedure or an open spine surgical procedure.

Functionally, the receiver-stimulator device comprises an ultrasound transducer to receive acoustic energy and transform it into electrical energy, an electrical circuit to transform the alternating electrical energy into a direct current or a pre-determined waveform, and electrodes to transfer the electrical field energy between an electrode pair to the tissue and to the surrounding area.

Additionally, a controller-transmitter device is adapted for directional, vibrational energy transmission emitted by the device to intersect the implanted receiver-stimulator. In an implanted version, the controller-transmitter device containing the transmitting transducer is implanted typically just beneath the skin in a subcutaneous space. If not implanted, the transducer portion of the transmitter would be placed over the skin directionally angled to the target region containing the receiver-stimulator with acoustic gel, or other means, used for coupling the acoustic energy to the skin.

In an alternative embodiment, the controller-transmitter device is incorporated into a device also providing conventional lead-based electrical stimulation, in a spinal cord stimulation system, wherein a conventional lead/electrode system would provide stimulus to directly connected regions of the spine using leads and transmitting vibrational energy to provide stimulation to regions of the spine where receiver-stimulators are implanted.

The controller-transmitter device would contain similar elements of most currently available stimulator systems including a power source, stimulation control and timing circuitry, physiologic sensing systems; in the implanted embodiment, a system to communicate with an outside console for data transmission, diagnostic, and programming functions typically through a radiofrequency (RF) link is provided. Additionally, the controller-transmitter device would contain an ultrasound amplifier and one or more ultrasound transducers to generate acoustic energy, and transmit such energy in the general direction of the receiver-stimulator implanted in the spine region. The duration, timing, and power of the acoustic energy transmission would be controlled as required, per tested parameters that are constructed for specific treatments for pain.

A single receiver-stimulator device is implanted in the epidural region of the spine as described above for single-region stimulation; alternatively it would be possible to implant a plurality of receiver-stimulator devices to stimulate either simultaneously by receiving the same transmitted acoustic energy or independently by responding only to acoustic energy with specific characteristics (i.e., of a certain frequency, amplitude, or by other modulation or encoding of the acoustic waveform) intended to energize only that specific device. This enables a much more robust utilization of site and region specific stimulation, which is not currently practical with current lead-based implementations whose electrode spacing is fixed on the lead set selected for use. Selecting multiple sites and regions for treatments would be greatly enhanced by eliminating the need to connect multiple electrode sites to the stimulation energy source by the use of multiple leads/wires connected to the electrodes or by attempting to anticipate the required spacing between electrodes.

These examples are representative but in no way limiting of the applications in which an electro-acoustic stimulator may be utilized in this invention to stimulate tissue in the spine to effect treatment of pain.

The delivery of ultrasound energy and, therefore, electrical stimulation could either be automatically triggered based on information received from an internal or external physiological sensor, or be based upon programmed settings, or be manually activated by the patient or other individuals. More specifically, the timing of the initiation of the delivery and/or the duration of the delivery and/or the energy content of the delivery and/or the information content of the delivery could be based upon sensor information or based upon programmed settings or be manually controlled.

Figure 8A:
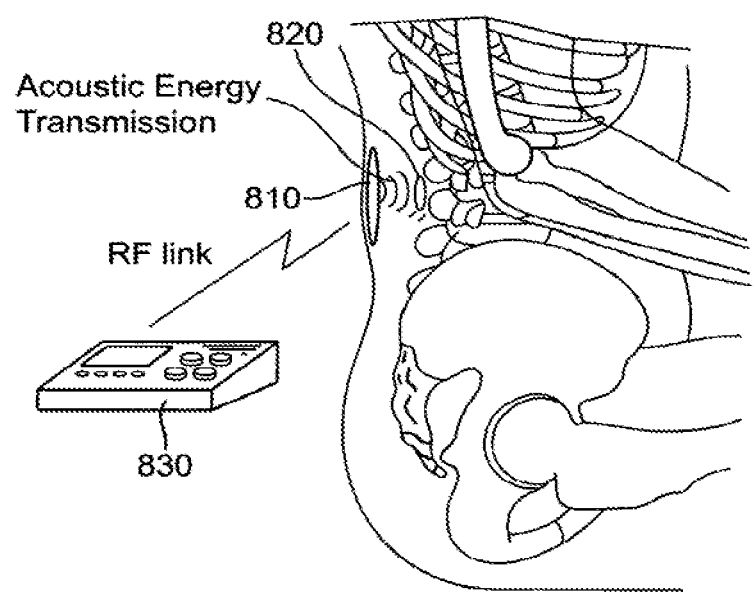
FIG. 8a is a schematic showing the leadless stimulation system using an implantable transmitter-controller for spinal cord stimulation.
Figure 8B:
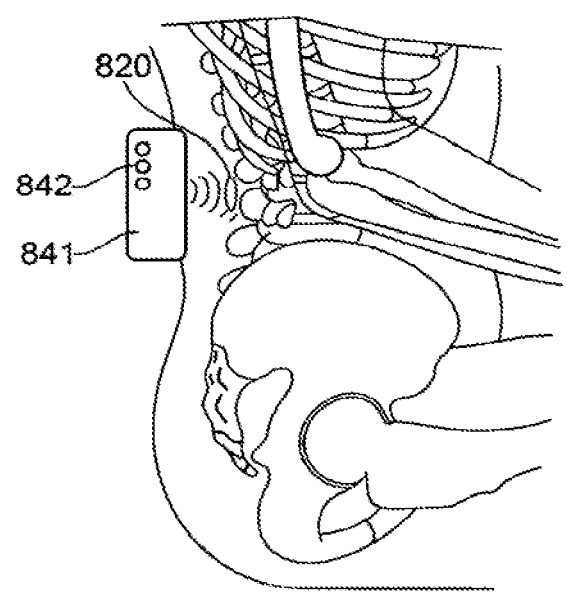
FIG. 8b is a schematic showing the leadless stimulation system using an externally applied transmitter-controller for spinal cord stimulation.

Examples of such an electro-acoustic stimulation system as a spine stimulator are illustrated in FIGS. 8a and 8b.

In FIG. 8a, a controller-transmitter device 810 containing circuitry to provide stimulation control and ultrasound transmission, plus means to communicate with an outside programmer 830 is implanted subcutaneously. It is situated such that the directional angle of the transmitted ultrasound beam would intersect the receiver-stimulator 820. Controller-transmitter 810, receiver-stimulator 820, and programmer 830 are similar to controller-transmitter 10, receiver-stimulator 20, and programmer 30, respectively, described earlier. An ultrasound signal is transmitted by this device through intervening tissue to the receiver-stimulator device 820 containing means to receive this acoustic energy and convert it into an electrical waveform which may then be applied to the attached electrodes. In FIG. 8a, this receiver-stimulator device 820 is shown embedded, in this one example, in the lumbar region of the spine. The receiver-stimulator device 820 is shown here as a small cylindrical or button-shaped device placed in the epidural region similar to current stimulator systems. Optionally, the receiver-stimulator 820 could be deployed into the epidural space affixed with an attaching coil or other method. Also optionally (not shown), the receiver-stimulator device 820 could be incorporated into a expandable or self-expanding mechanical mesh that would stay located in the tissue by means of spring tension similar to a stent placement in a vascular application but rather held in place between tissue sections of the spine.

In FIG. 8b, an externally applied controller-transmitter device 841 containing circuitry to provide stimulation therapy control and ultrasound transmission, plus control means 842 to allow the patient or operator to directly adjust ultrasound output based on desired therapy parameters including, at least, amplitude, pulse duration, and pulse repetition frequency, to produce effective pain relief. The external transmitter 841 may be handheld, or worn on the body, attached by a belt, harness, or the like. The external controller-transmitter 841 is similar to the implantable controller-transmitter device described previously, containing at the minimum an adjustable pulse/frequency generator, ultrasound amplifier, ultrasound transmitter, and battery. Optionally, the battery may be a rechargeable type. It is situated such that the directional angle of the transmitted ultrasound beam would intersect the receiver-stimulator 820. An ultrasound signal is transmitted by this device through intervening tissue to the receiver-stimulator device 820 containing means to receive this acoustic energy and convert it into an electrical waveform which may then be applied to the attached electrodes. In FIG. 8b, this receiver-stimulator device 820 is shown embedded, in this one example, in the lumbar region of the spine. The details of this system are similar to those shown in FIG. 1.

Example 3: GI Stimulation

Figure 9B:
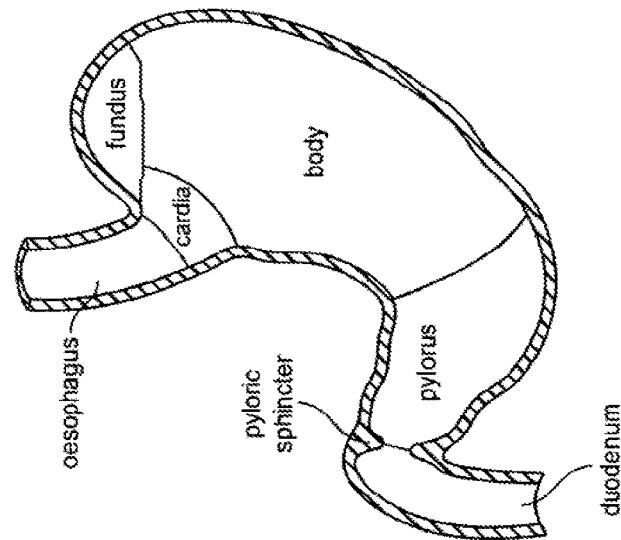
FIGS. 9a and 9b are schematics showing the basics of the gastrointestinal system anatomy.
Figure 9A:
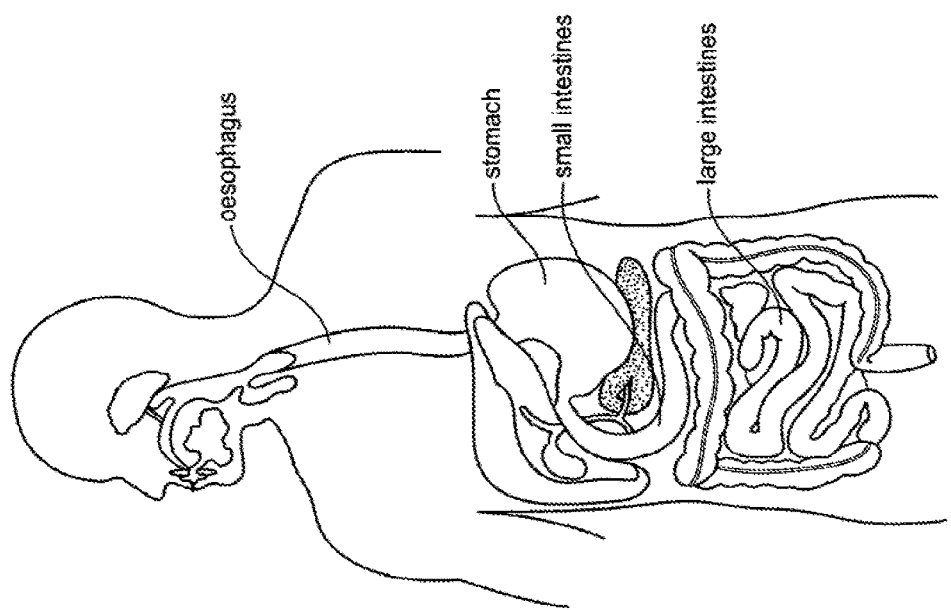

As described in the Background section and illustrated in FIGS. 9a and 9b, the gastrointestinal system is essentially a long tube running from the mouth to the anus consisting of four main sections including the oesophagus, the stomach, the small intestines, and the large intestines. These specialized sections are capable of digesting material place in the mouth and extracting components useful to the body as the material passes through the system. Material that can not be used or that has been processed is expelled from the end of the tube at the anus. The system is under hormonal control, with the presence of food in the mouth triggering off a cascade of hormonal actions; when there is food in the stomach, different hormones activate acid secretion, increased gut motility, enzyme release etc. As illustrated in FIG. 9b, the stomach is a 'j'-shaped organ, with two openings—the esophageal and the duodenal, and four regions—the cardia, fundus, body and pylorus. Each region performs different functions; the fundus collects digestive gases, the body secretes pepsinogen and hydrochloric acid, and the pylorus is responsible for mucus, gastrin and pepsinogen secretion. The body uses this arrangement to process food and supply nutrients to the system.

A leadless receiver-stimulator would be placed using transesophageal, percutaneous or direct surgical access. For the transesophageal approach, an endoscopy style device swallowed by the patient can be used to access the gastrointestinal system and the receiver-stimulator could be placed in the desired location. Alternatively, a percutaneous needle or laparoscopic delivery technique is used to access the gastrointestinal tissue, a miniaturized receiver-stimulator device, disposed within the delivery needle or within the laparoscopy device, is implanted into gastrointestinal tissue or attached to the desired location on the external surface of gastrointestinal tissue. Currently known techniques and tools for surgical access and probing of gastrointestinal tissue could be adapted to facilitate delivery of the receiver-stimulator to these locations; the receiver-transmitter may incorporate means to provide permanent attachment to the implant site including possibly helical coils, clips, barbs, tines, or the like or would be adapted in form to surround the gastrointestinal tissue as a wrap or along the length of the gastrointestinal tissue.

Functionally, the receiver-stimulator device comprises an ultrasound transducer to receive acoustic energy and transform it into electrical energy, an electrical circuit to transform the alternating electrical energy into direct current, and electrodes to transfer the electrical field energy between an electrode pair to the gastrointestinal tissue.

Additionally, a controller-transmitter device is adapted for directional, vibrational energy transmission emitted by the device to intersect the implanted receiver-stimulator. In an implanted version, the controller-transmitter device containing the transmitting transducer is implanted typically just beneath the skin in a subcutaneous space. If not implanted, the transducer portion of the transmitter would be placed on the skin directionally angled to the target region containing the receiver-stimulator with acoustic gel, or other means, used for coupling the acoustic energy to the skin.

In an alternative embodiment, the controller-transmitter device is incorporated into a device also providing conventional lead-based electrical stimulation, in a gastrointestinal tissue stimulation system wherein a conventional lead/electrode system would provide stimulus to directly connected regions of the gastrointestinal tissue using leads and transmitting vibrational energy to provide stimulation to regions of the gastrointestinal tissue where receiver-stimulators are implanted.

The controller-transmitter device would contain similar elements of most currently available stimulator systems, including a power source, stimulation control and timing circuitry, physiologic sensing systems; and in the implanted embodiment, a system to communicate with an outside console for data transmission, diagnostic, and programming functions typically through a radiofrequency (RF) link is provided. Additionally, the controller-transmitter device would contain an ultrasound amplifier and one or more ultrasound transducers to generate acoustic energy, and transmit such energy in the general direction of the receiver-stimulator implanted in the body. The duration, timing, and power of the acoustic energy transmission would be controlled as required, per tested parameters that are constructed for specific treatments.

A single receiver-stimulator device is implanted with the electrodes in contact or close proximity to the gastrointestinal tissue, as described above, for single-region stimulation; alternatively, it would be possible to implant a plurality of receiver-stimulator devices to stimulate either simultaneously by receiving the same transmitted acoustic energy or independently by responding only to acoustic energy of a specific character (i.e., of a certain frequency, amplitude, or by other modulation or encoding of the acoustic waveform) intended to energize only that specific device. This enables a much more robust utilization of site and region specific stimulation not currently practical with current lead-based implementations whose electrode spacing is fixed on the lead set selected for use and may not adapt itself to the structure of the gastrointestinal tissue. Selecting multiple sites and regions for treatments would be greatly enhanced by eliminating the need to connect multiple electrode sites to the stimulation energy source by the use of multiple leads/wires connected to the electrodes or by attempting to anticipate the required spacing between electrodes.

The delivery of ultrasound energy and, therefore, electrical stimulation could either be automatically triggered based on information received from an internal or external physiological sensor, or be based upon programmed settings, or be manually activated by the patient or other individuals. More specifically, the timing of the initiation of the delivery and/or the duration of the delivery and/or the energy content of the delivery and/or the information content of the delivery could be based upon sensor information or based upon programmed settings or be manually controlled.

Figure 10A:
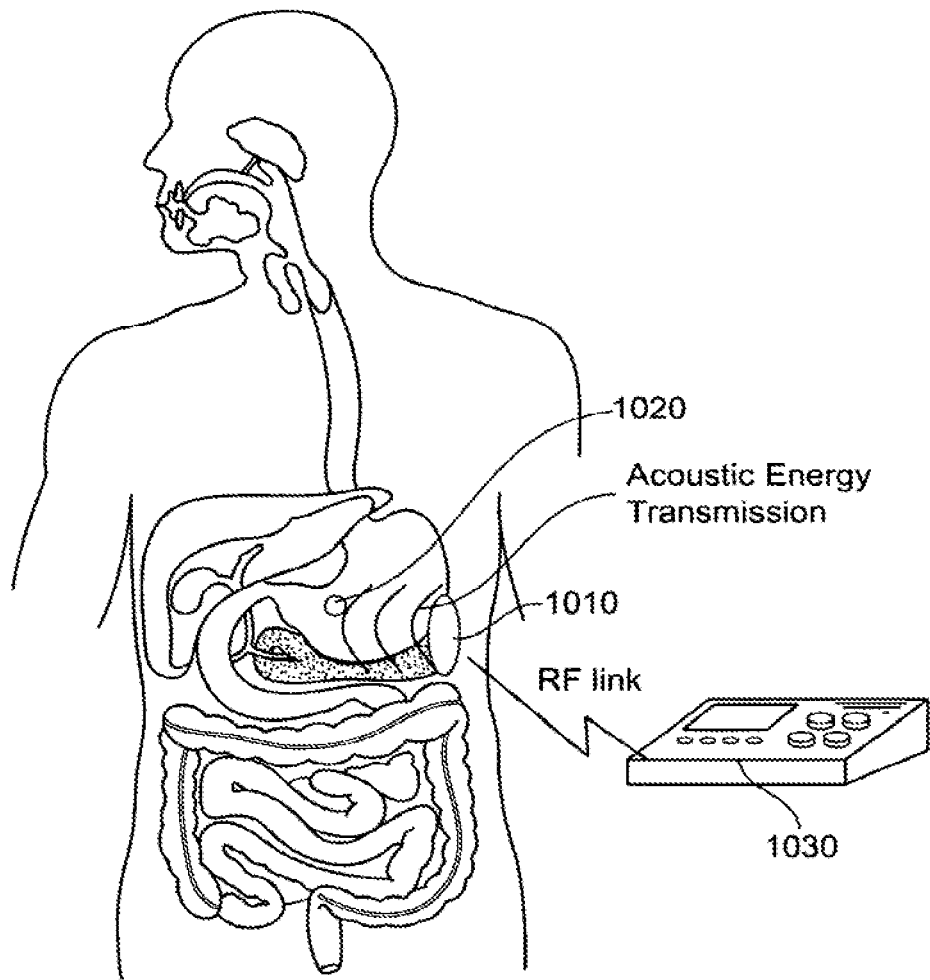
FIG. 10a is a schematic showing the leadless stimulation system using an implantable controller-transmitter for stimulation of the stomach.
Figure 10B:
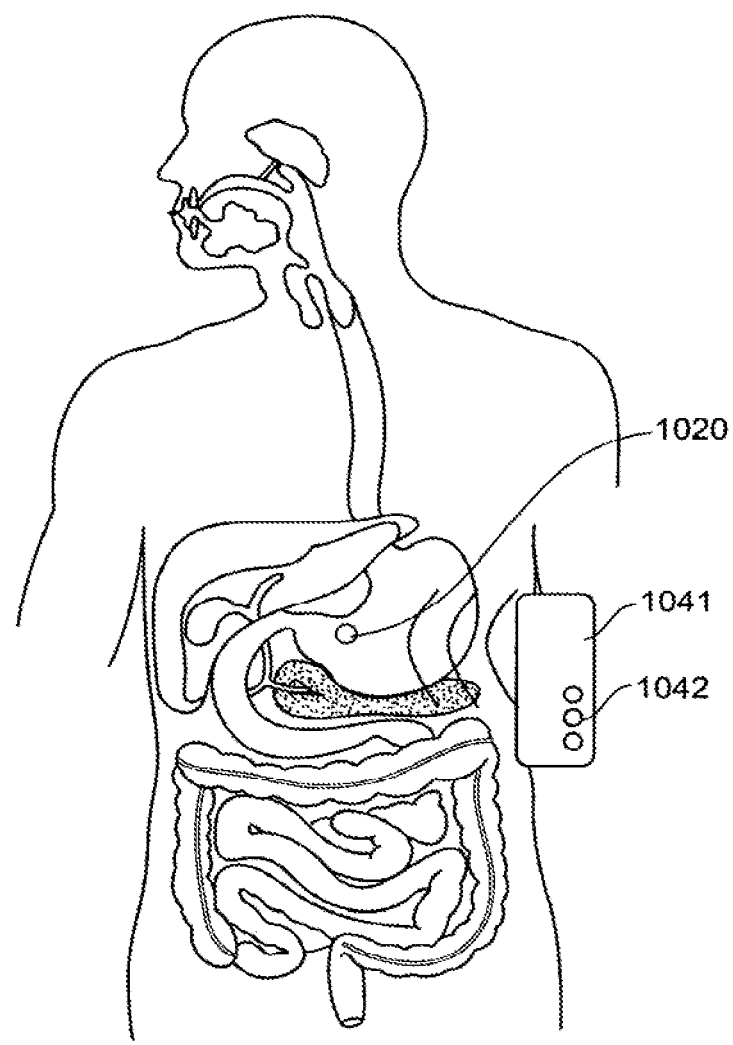
FIG. 10b is a schematic showing the leadless stimulation system using an externally applied controller-transmitter for stimulation of the stomach.

Examples of such an electro-acoustic stimulation system as a gastrointestinal tissue stimulator are illustrated in FIGS. 10a and 10b.

In FIG. 10a, a controller-transmitter device 1010 containing circuitry to provide stimulation control and ultrasound transmission, plus means to communicate with an outside programmer 1030 is implanted subcutaneously. It is situated such that the directional angle of the transmitted ultrasound beam would intersect the receiver-stimulator 1020. Controller-transmitter 1010, receiver-stimulator 1020, and programmer 1030 are similar to controller-transmitter 10, receiver-stimulator 20, and programmer 30, respectively, described earlier. An ultrasound signal is transmitted by this device through intervening body tissue to the receiver-stimulator device 1020 containing means to receive this acoustic energy and convert it into an electrical waveform which may then be applied to the attached electrodes. In FIG. 10a this receiver-stimulator device 1020 is shown embedded, in this one example, in the pylorus region of the stomach. The receiver-stimulator device 20 is shown here as a small cylindrical or button-shaped device placed on the gastrointestinal tissue in similar ways that current stimulator systems apply electrodes to stomach tissues. Optionally, the receiver-stimulator 1020 could be deployed onto the gastrointestinal tissue or in proximity to the gastrointestinal tissue affixed with an attaching coil or other method. Also optionally (not shown), the receiver-stimulator device 1020 could be incorporated into a expandable or self-expanding mechanical mesh that would stay located in the gastrointestinal tissue by means of spring tension similar to a stent placement in a vascular application but rather held in place between gastrointestinal tissue sections near the gastrointestinal tissue.

In FIG. 10*b*, an externally applied controller-transmitter device 1041 containing circuitry to provide stimulation therapy control and ultrasound transmission, plus control means 1042 to allow the patient or operator to directly adjust ultrasound output based on desired therapy parameters including at least amplitude, pulse duration, and pulse repetition frequency, to produce an effective control of the gastrointestinal tissue. The external transmitter 1041 may be handheld, or worn on the body, attached by a belt, harness, or the like. The external controller-transmitter 1041 is similar to the implantable controller-transmitter device described previously, containing at the minimum an adjustable pulse/frequency generator, ultrasound amplifier, ultrasound transmitter, and battery. Optionally, the battery may be a rechargeable type. It is situated such that the directional angle of the transmitted ultrasound beam would intersect the receiver-stimulator 1020. An ultrasound signal is transmitted by this device through intervening body tissue to the receiver-stimulator device 1020 containing means to receive this acoustic energy and convert it into an electrical waveform which may then be applied to the attached electrodes. In FIG. 10*b*, this receiver-stimulator device 1020 is shown embedded, in this one example, in the pylorus region of the stomach and could be used with appropriate selection of stimulation parameters for obesity treatment.

Example 4: Spine Stimulation

Figure 11:
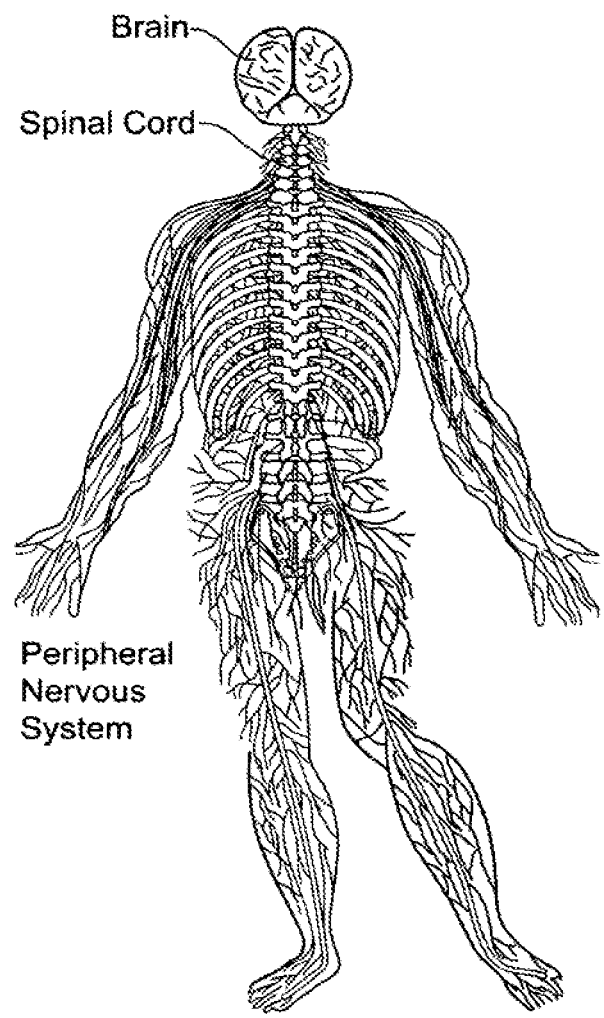
FIG. 11 is a schematic showing the basics of the nervous system anatomy.

As illustrated in FIG. 11 and described in the Background section, the central nervous system is pervasive throughout the body with individual nerves and nerve bundles reaching to all bodily functions. The PNS consists of the cervical, thoracic, lumbar, and sacral nerve trunks leading away from the spine to all regions of the body. The peripheral nervous system also includes cranial nerves. Sensory and control signals travel between the brain and other regions of the body using this network of nerves that all travel along the spinal cord.

A leadless pulse stimulator would be applied percutaneously or surgically. Utilizing a percutaneous needle delivery technique to access the nerve, a miniaturized receiver-stimulator device disposed within the delivery needle is implanted into tissue or attached to the desired location on the nerve. Various techniques and tools for surgical access and probing of nerve tissue are commonly known. These could be adapted to facilitate delivery of the receiver-stimulator to these locations; the receiver-transmitter may incorporate means to provide permanent attachment to the implant site including possibly helical coils, barbs, tines, or the like or could be adapted in form to surround the nerve as a wrap or along the longitudinal length of the nerve.

Functionally, the receiver-stimulator device comprises an ultrasound transducer to receive acoustic energy and transform it into electrical energy, an electrical circuit to transform the alternating electrical energy into a direct current or a pre-determined waveform, and electrodes to transfer the electrical field energy between an electrode pair to the nerve.

Additionally, a controller-transmitter device is adapted for directional, vibrational energy transmission emitted by the device to intersect the implanted receiver-stimulator. In an implanted version, the controller-transmitter device containing the transmitting transducer is implanted typically just beneath the skin in a subcutaneous space. If not implanted, the transducer portion of the transmitter would be placed over the skin directionally angled to the target region containing the receiver-stimulator with acoustic gel, or other means, used for coupling the acoustic energy to the skin.

In an alternative embodiment, the controller-transmitter device is incorporated into a device also providing conventional lead-based electrical stimulation, in a nerve stimulation system wherein a conventional lead/electrode system would provide stimulus to directly connected regions of the nerve using leads and transmitting vibrational energy to provide stimulation to regions of the nerve where receiver-stimulators are implanted.

The controller-transmitter device would contain similar elements of most currently available stimulator systems including a power source, stimulation control and timing circuitry, physiologic sensing systems, and in the implanted embodiment, a system to communicate with an outside console for data transmission, diagnostic, and programming functions typically through a radiofrequency (RF) link is provided. Additionally, the controller-transmitter device would contain an ultrasound amplifier and one or more ultrasound transducers to generate acoustic energy, and transmit such energy in the general direction of the receiver-stimulator implanted in the body. The duration, timing, and power of the acoustic energy transmission would be controlled as required, per tested parameters that are constructed for specific treatments.

A single receiver-stimulator device is implanted with the electrodes in contact or close proximity to the nerve, as described above, for single-region stimulation; alternatively, it would be possible to implant a plurality of receiver-stimulator devices to stimulate either simultaneously by receiving the same transmitted acoustic energy or independently by responding only to acoustic energy of a specific character (i.e., of a certain frequency, amplitude, or by other modulation or encoding of the acoustic waveform) intended to energize only that specific device. This enables a much more robust utilization of site and region specific stimulation not currently practical with current lead-based implementations whose electrode spacing is fixed on the lead set selected for use and may not adapt itself to the structure of the nerve. Selecting multiple sites and regions for treatments would be greatly enhanced by eliminating the need to connect multiple electrode sites to the stimulation energy source by the use of multiple leads/wires connected to the electrodes or by attempting to anticipate the required spacing between electrodes.

The delivery of ultrasound energy and, therefore, electrical stimulation could either be automatically triggered based on information received from an internal or external physiological sensor, or be based upon programmed settings, or be manually activated by the patient or other individuals. More specifically, the timing of the initiation of the delivery and/or the duration of the delivery and/or the energy content of the delivery and/or the information content of the delivery could be based upon sensor information or based upon programmed settings or be manually controlled.

Figure 11A:
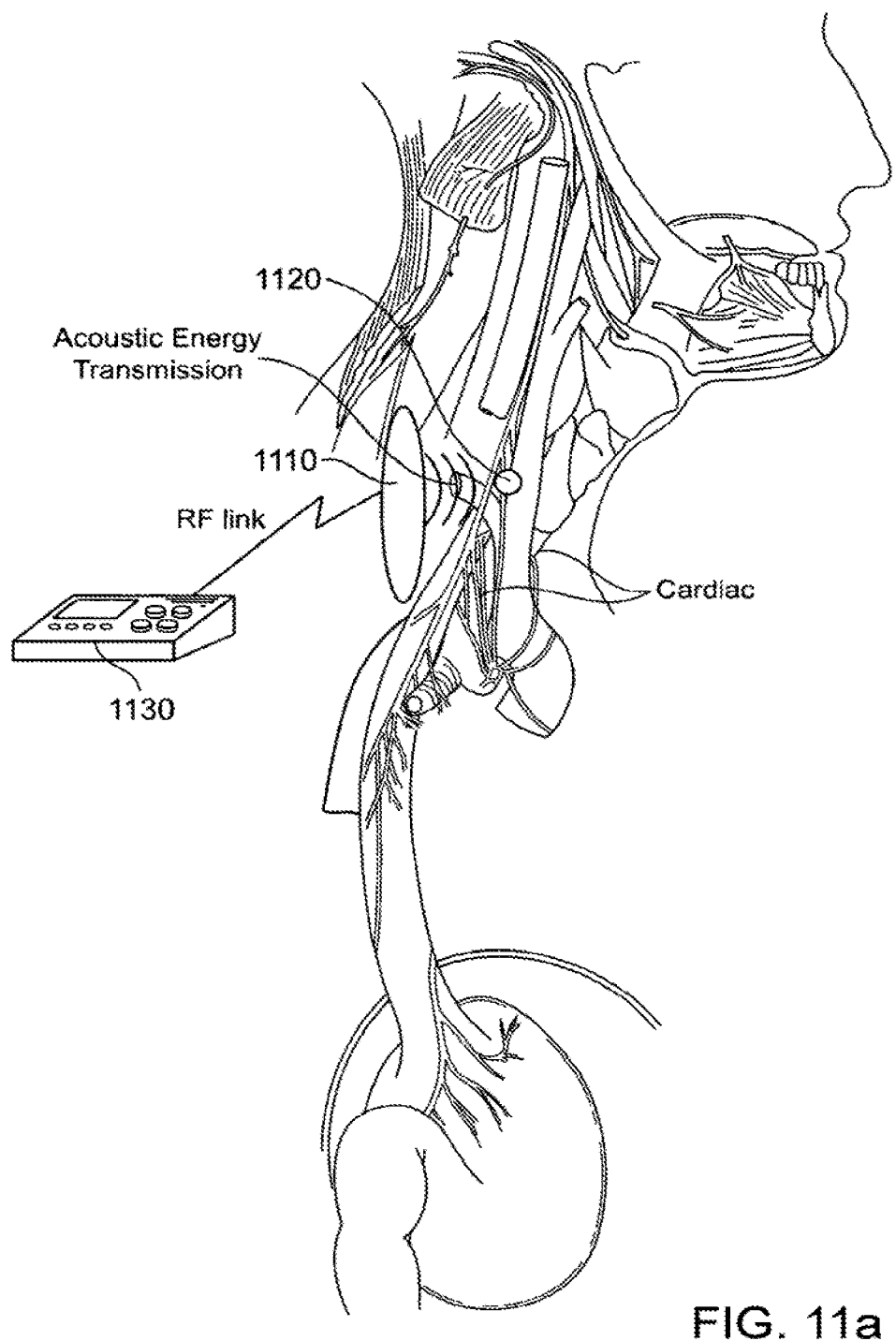
FIG. 11a is a schematic showing the leadless stimulation system using an implantable controller-transmitter for stimulation of a peripheral branch of the vagus nerve.
Figure 11B:
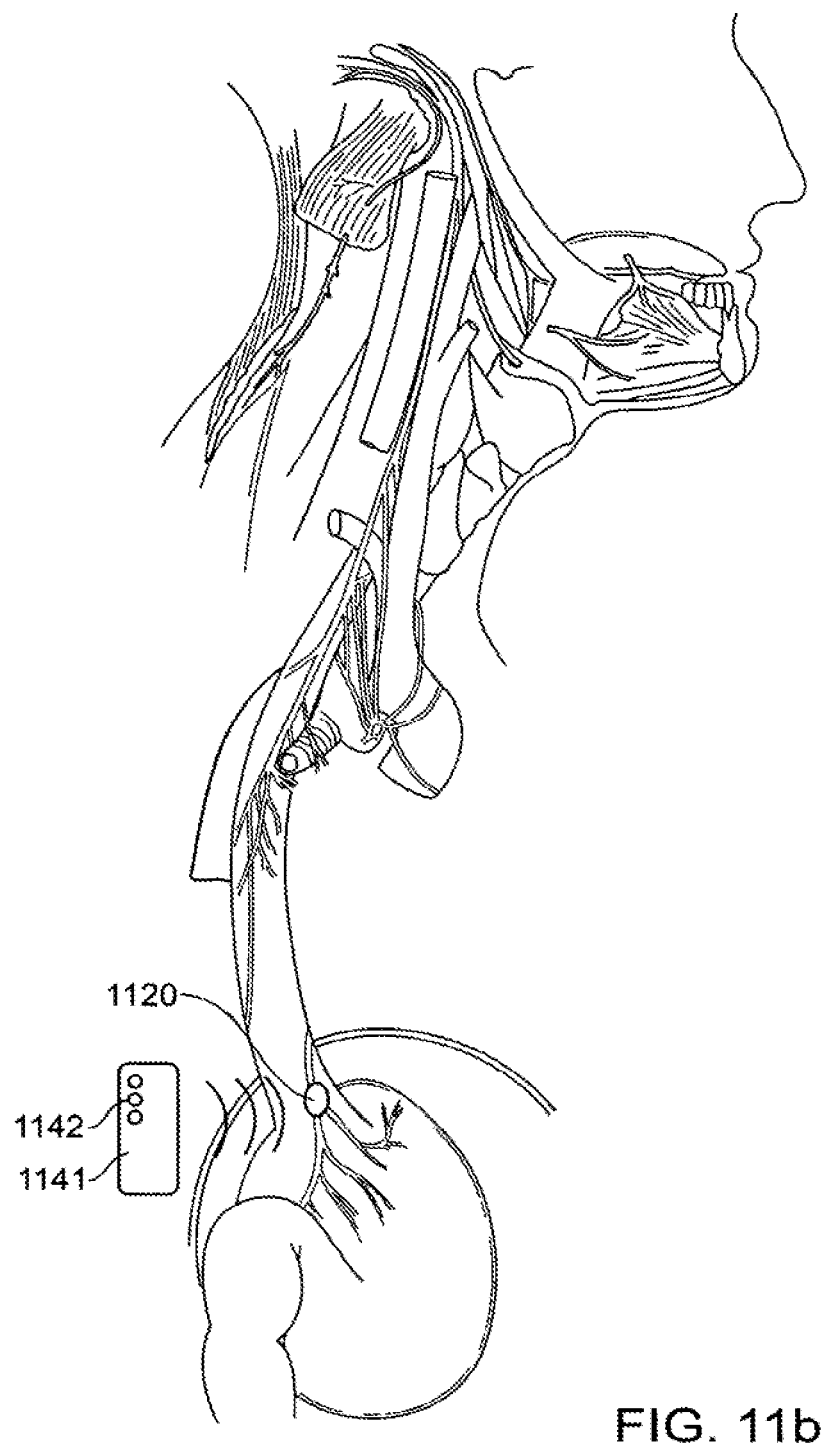
FIG. 11b is a schematic showing the leadless stimulation system using an externally applied controller-transmitter for stimulation of a peripheral branch of the vagus nerve.

Examples of such an electro-acoustic stimulation system as a nerve stimulator are illustrated in FIGS. 11*a* and 11*b*.

In FIG. 11*a*, a controller-transmitter device 1110 containing circuitry to provide stimulation control and ultrasound transmission, plus means to communicate with an outside programmer 1130 is implanted subcutaneously. It is situated such that the directional angle of the transmitted ultrasound beam would intersect the receiver-stimulator 1120. Controller-transmitter 1110, receiver-stimulator 1120, and programmer 1130 are similar to controller-transmitter 10, receiver-stimulator 20, and programmer 30, respectively, described earlier. An ultrasound signal is transmitted by this device through intervening tissue to the receiver-stimulator device 1120 containing means to receive this acoustic energy and convert it into an electrical waveform which may then be applied to the attached electrodes. In FIG. 11b, this receiver-stimulator device 1120 is shown embedded, in this one example, in the neck region and attached to a peripheral branch of the vagus nerve bundle. The receiver-stimulator device 1120 is shown here as a small cylindrical or button-shaped device placed on the nerve in similar ways that current stimulator systems apply electrodes to nerves. Optionally, the receiver-stimulator 1120 could be deployed onto the nerve or in proximity to the nerve affixed with an attaching coil or other method. Also optionally (not shown), the receiver-stimulator device 1120 could be incorporated into a expandable or self-expanding mechanical mesh that would stay located in the tissue by means of spring tension similar to a stent placement in a vascular application but rather held in place between tissue sections near the nerve.

In FIG. 11b, an externally applied controller-transmitter device 1141 containing circuitry to provide stimulation therapy control and ultrasound transmission, plus control means 1142 to allow the patient or operator to directly adjust ultrasound output based on desired therapy parameters including, at least, amplitude, pulse duration, and pulse repetition frequency, to produce an effective control of the nerve. The external transmitter 1141 may be handheld, or worn on the body, attached by a belt, harness, or the like. The external controller-transmitter 1141 is similar to the implantable controller-transmitter device described previously, containing, at the minimum, an adjustable pulse/frequency generator, ultrasound amplifier, ultrasound transmitter, and battery. Optionally, the battery may be a rechargeable type. It is situated such that the directional angle of the transmitted ultrasound beam would intersect the receiver-stimulator 1120. An ultrasound signal is transmitted by this device through intervening tissue to the receiver-stimulator device 1120 containing means to receive this acoustic energy and convert it into an electrical waveform which may then be applied to the attached electrodes. In FIG. 11b, this receiver-stimulator device 1120 is shown embedded, in this one example, in a branch of the vagus nerve in the region of the stomach as a treatment for obesity.

Example 5: Brain Stimulation

Figure 12:
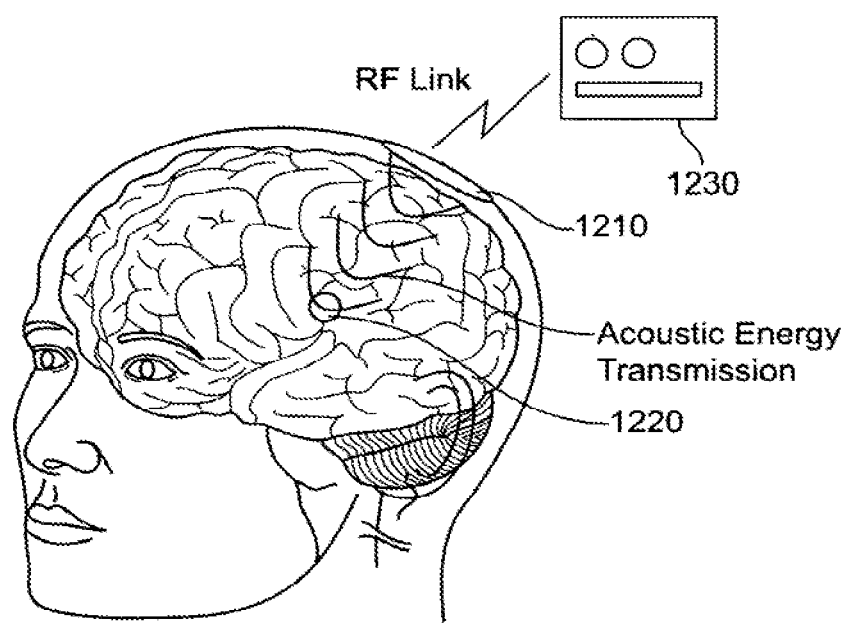
FIG. 12 is a schematic showing the leadless stimulation system for deep brain stimulation.

An example of an electro-acoustic stimulation system as a brain stimulator is illustrated in FIG. 12.

In FIG. 12, controller-transmitter device 1210 containing circuitry to provide stimulation control and ultrasound transmission, plus means to communicate with the outside programmer 1230 is implanted in the skull, either subcutaneously between the skull and the skin or as a replacement for skull bone removed during access of the cranial area. It is situated such that the directional angle of the transmitted ultrasound beam would intersect the receiver-stimulator 1220. Controller-transmitter 1210, receiver-stimulator 1220, and programmer 1230 are similar to controller-transmitter 10, receiver-stimulator 20, and programmer 30, respectively, described earlier. An ultrasound signal is transmitted by this device through intervening tissue to the receiver-stimulator device 1220 containing means to receive this acoustic energy and convert it into an electrical waveform which may then be applied to the attached electrodes. In FIG. 12 this receiver-stimulator device 1220 is shown embedded, in this one example, in a deep brain location near the thalamus. The receiver-stimulator device 1220 is shown here as a small cylindrical or button-shaped device that would be affixed to the brain with an attaching coil or other method, similar to the means by which electrical lead wires are fixed to the brain in current stimulator systems. Optionally (not shown), the receiver-stimulator 1220 could be deployed into the brain tissue. Also optionally (not shown), the receiver-stimulator device 1220 could be incorporated into a expandable or self-expanding mechanical mesh that would stay located in the tissue by means of spring tension similar to a stent placement in a vascular application but rather held in place between tissue sections of the brain.

Example 6: Cochlear Stimulation

Figure 13:
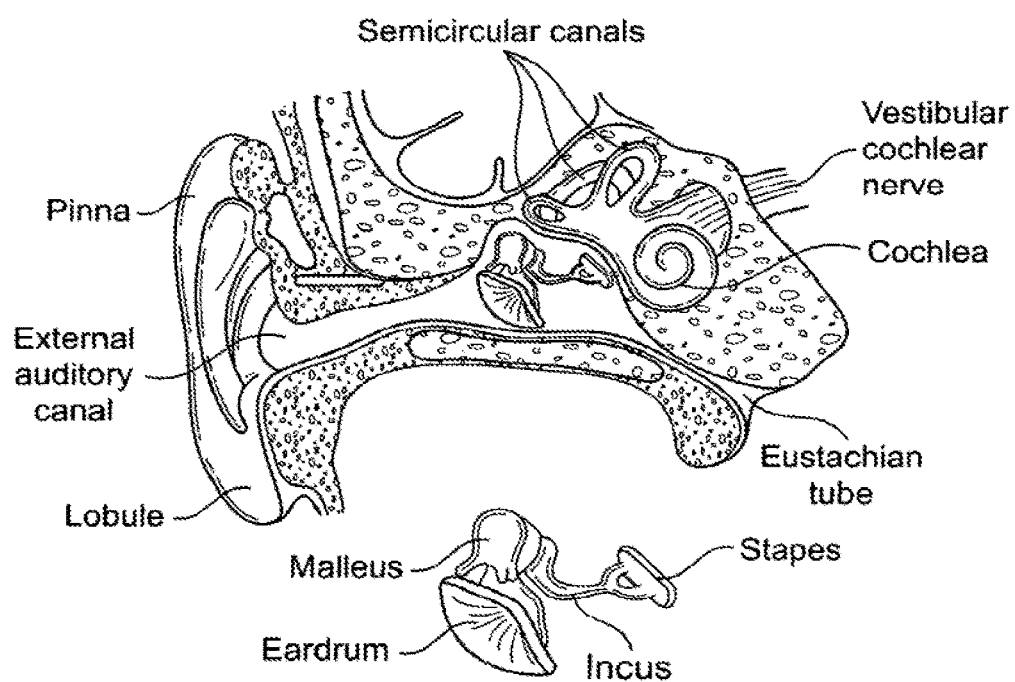
FIG. 13 is a schematic showing the basics of the ear/hearing anatomy.
Figure 13A:
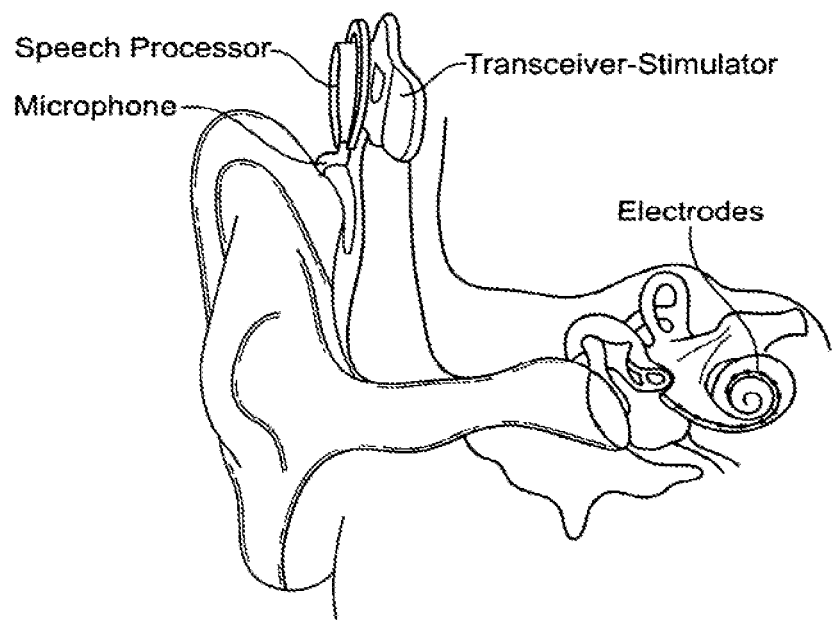
FIGS. 13a and 13b are schematics showing a typical cochlear implant system using an external microphone and sound-speech processor and an implantable transceiver-stimulator and electrodes for stimulation in the cochlea of the ear.
Figure 13B:
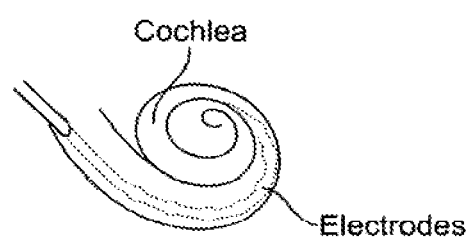

As described in the Background section and illustrated in FIGS. 13, 13a and 13b the hearing system is an anatomical structure that begins at the ear canal. Sound travels through the canal to the ear drum which vibrates and sets in motion bones in the inner ear. This motion causes the fluid in the cochlea to move small hair cells. The hair cells transduce this movement into electrical impulses in the cochlear nerve which sends the impulses to the brain, which then interprets the impulses as sound.

Utilizing a percutaneous needle delivery technique to access the cochlea, a miniaturized receiver-stimulator device disposed within the delivery needle is implanted into the cochlea. Various techniques and tools for surgical access and probing of the cochlea that are currently used, or have been described in the literature, could be adapted to facilitate delivery of the receiver-stimulator to these locations; the receiver-transmitter may incorporate means to provide permanent attachment to the implant site including possibly helical coils, barbs, tines, or the like or would be adapted in form to expand/spring against the tissue to maintain its position.

Functionally, the receiver-stimulator device comprises an ultrasound transducer to receive acoustic energy and transform it into electrical energy, an electrical circuit to transform the alternating electrical energy into a direct current, and electrodes to transfer the electrical field energy between an electrode pair to the cochlea.

Additionally, a controller-transmitter device is adapted for directional, vibrational energy transmission emitted by the device to intersect the implanted receiver-stimulator. In an external version of the controller-transmitter, the transducer portion of the transmitter would be placed over the skin directionally angled to the target region containing the receiver-stimulator with acoustic gel, or other means, used for coupling the acoustic energy to the skin. In an implanted version, the controller-transmitter device containing the transmitting transducer is implanted typically just beneath the skin in a subcutaneous space.

The controller-transmitter device would contain elements similar to most currently available cochlear implant system (CIS), including a power source, stimulation control and timing circuitry. In its external embodiment, it would be possible to integrate the function of a sound-speech processor into a single enclosure with the controller-transmitter, or still yet integrate the function of the microphone, the sound-speech processor, and the controller transmitter into a single enclosure. In its implantable embodiment, the controller-transmitter would communicate with an outside sound-speech processor component via RF, electromagnetic, or acoustic means for data transmission of device function. Additionally, the controller-transmitter device would contain an ultrasound amplifier and one or more ultrasound transducers to generate acoustic energy, and transmit such energy in the general direction of the receiver-stimulator implanted in the body. The duration, timing, and power of the acoustic energy transmission would be controlled as required, per sound-speech processing parameters that are constructed for specific sound sensations.

A single receiver-stimulator device is implanted with the electrodes positioned within the cochlea of the ear. The single receiver-stimulator device may be adapted to contain multiple electrodes dispersed through the cochlea. Alternatively, it would be possible to implant a plurality of miniaturized receiver-stimulator devices throughout the cochlea to stimulate either simultaneously by receiving the same transmitted acoustic energy or independently by responding only to acoustic energy of a specific character (i.e., of a certain frequency, amplitude, or by other modulation or encoding of the acoustic waveform) intended to energize only that specific device. This enables a much more robust utilization of site and region specific stimulation not currently practical with current lead-based implementations whose electrode spacing is fixed on the lead set selected for use and may not adapt itself to the structure of the cochlea. Selecting multiple sites and regions for treatments would be greatly enhanced by eliminating the need to connect multiple electrode sites to the stimulation energy source by anticipating the required spacing between electrodes.

These examples are representative and in no way limiting the applications in which a stimulator based on using vibrational energy may be utilized in this invention to stimulate within the cochlea of the ear to treat provide a sound sensation to the brain.

The delivery of ultrasound energy and, therefore, electrical stimulation would be automatically triggered based on sound information received through a microphone and through a sound-speech processor. More specifically, the timing of the initiation of the delivery and/or the duration of the delivery and/or the energy content of the delivery and/or the information content of the delivery would be based upon processing sound picked up through this CIS system.

Figure 14A:
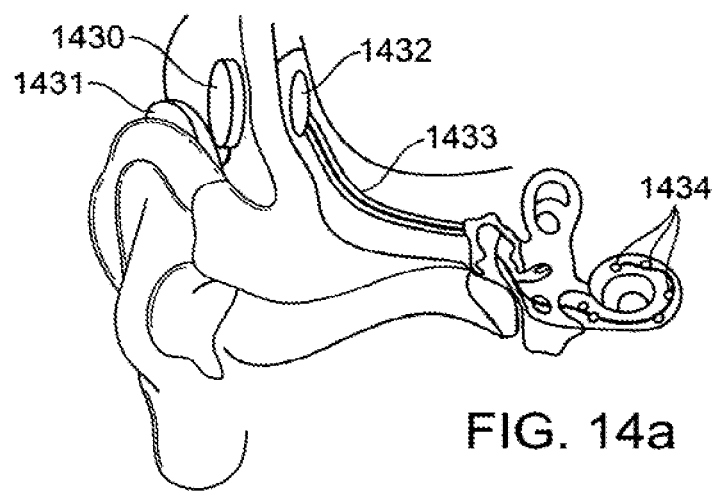
FIGS. 14a, 14b, and 14c are schematics showing the leadless stimulation system of the present invention with an externally applied acoustic transmitter-controller and implanted receiver-stimulators for stimulation in the cochlea of the ear.
Figure 14B:
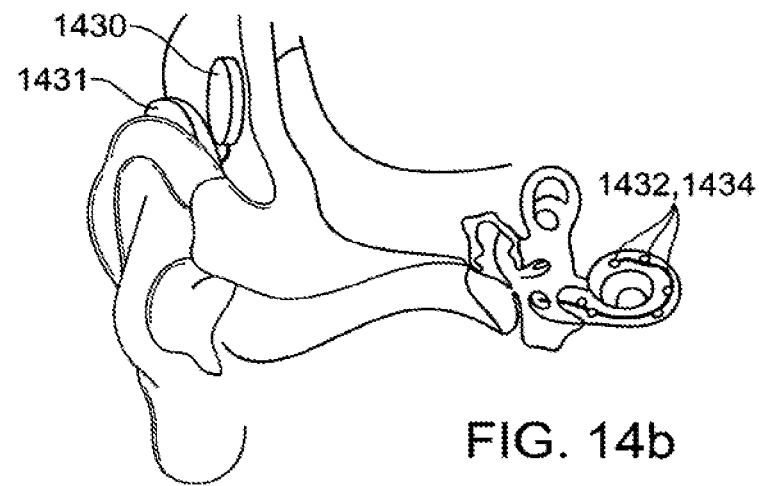
Figure 14C:
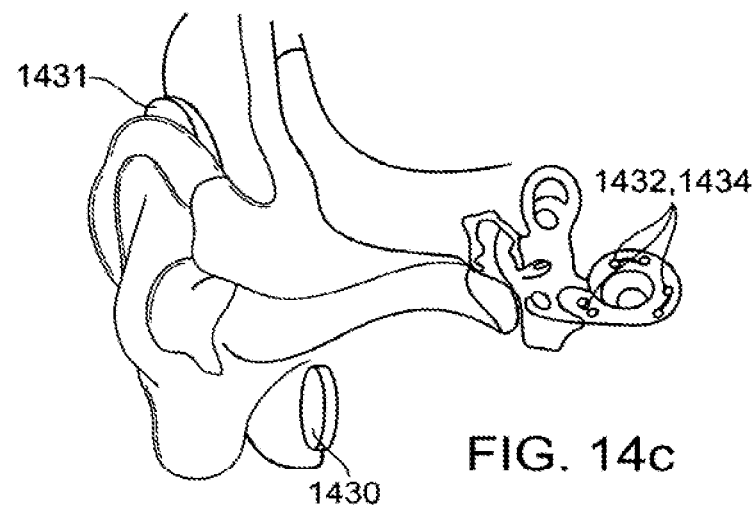

Examples of such an acoustic CIS system as a cochlea stimulator are illustrated in FIGS. 14a-14c.

In FIG. 14a, a sound processing device 1431 containing a sound microphone, amplifier, sound processing circuitry, ultrasound amplifier, and battery circuitry to receive ambient sound is shown mounted over the ear. The sound processing device 1431 is connected via a lead/cable to one or more controller-transmitter transducers 1430, shown here mounted to the outside surface of the skull, on the scalp. It should be appreciated that the functional components of the sound processor and controller-transmitter could be partitioned as desired into one or more enclosures with the important function of the acoustic energy transfer being applied through a transmission transducer directly to the external surface of the body. A receiver-stimulator consisting of a receiver 1432, a lead connection 1433, and electrodes 1434 is implanted in the body. The receiver 1432 is situated such that the directional angle of the transmitted ultrasound beam from the controller-transmitter transducer 1430 would intersect the receiver 1432. An ultrasound signal is transmitted by controller-transmitter transducer 1430 through intervening tissue to the receiver 1432 containing means to receive this acoustic energy and convert it into an electrical waveform which may then be applied to the attached electrodes. The sound processing circuitry of sound processing device 1431 would separate the sound into multiple channels associated with the multiple electrodes 1434 implanted in the cochlea; the multiple channels of information would then be encoded into the transmitted ultrasound signal through an appropriate modulation technique. Thus, the transmitted modulated ultrasound signal will comprise an energy component to provide power to the implanted circuitry and an information component to provide signal content to multiple electrodes Implanted receiver 1432 contains both an ultrasound receiving transducer and the necessary electronics circuitry to convert the acoustic energy into electrical power, to demodulate the signal content within the ultrasound signal into one or multiple signal channels, and one or multiple circuits to process the signal content and apply the product to the electrodes 1434, which are disposed on an implantable lead 33, whose distal end is placed within the cochlea.

In FIG. 14b, an alternative embodiment of the present invention is illustrated. In FIG. 14b, sound processing device 1431 containing a sound microphone, amplifier, sound processing circuitry, ultrasound amplifier, and battery circuitry to receive ambient sound is shown mounted over the ear. The sound processing device 1431 is connected via a lead/cable to one or more controller-transmitter transducers 1430, shown here mounted to the outside surface of the skull, on the scalp. A receiver-stimulator consisting of a receiver 1432 and electrodes 1434 is implanted fully within the cochlea. The receiver 1432 is situated such that the directional angle of the transmitted ultrasound beam from the controller-transmitter transducer 1430 would intersect the receiver 1432. An ultrasound signal is transmitted by controller-transmitter transducer 1430 through intervening tissue to the receiver 1432 containing means to receive this acoustic energy and convert it into an electrical waveform which may then be applied to the attached electrodes. The sound processing circuitry of sound processing device 1431 would separate the sound into multiple channels associated with the multiple electrodes 1434 implanted in the cochlea; the multiple channels of information would then be encoded into the transmitted ultrasound signal through an appropriate modulation technique. Thus, the transmitted modulated ultrasound signal will comprise an energy component to provide power to the implanted circuitry and an information component to provide signal content to multiple electrodes Implanted receiver 1432 contains both an ultrasound receiving transducer and the necessary electronic circuitry to convert the acoustic energy into electrical power, to demodulate the signal content within the ultrasound signal into one or multiple signal channels, and one or multiple circuits to process the signal content and apply the output to the electrodes 1434 which are disposed on receiver-stimulator, where the entirety of the receiver-stimulator is disposed within the cochlea.

In FIG. 14c, an alternative embodiment of the present invention is illustrated. In FIG. 14c, a sound processing device 1431 containing a sound microphone, amplifier, sound processing circuitry, ultrasound amplifier, and battery circuitry to receive ambient sound is shown mounted over the ear. The sound processing device 1431 is connected via a lead/cable to one or more controller-transmitter transducers 1430, shown here mounted to the outside surface of the head, beneath the ear. It should be appreciated that the functional components of the sound processor and controller-transmitter could be partitioned as desired into one or more enclosures with the important function of the acoustic energy transfer being applied through a transmission transducer directly to the external surface of the body. Multiple receiver-stimulators consisting of a receiver 1432 and electrodes 1434 are implanted in the cochlea. The individual receiver-stimulators are situated such that the directional angle of the transmitted ultrasound beam from the controller-transmitter transducer 1430 would intersect the multiple receivers 1432. An ultrasound signal is transmitted by controller-transmitter transducer 1430 through intervening tissue to the receivers 1432 containing means to receive this acoustic energy and convert it into an electrical waveform which may then be applied to the attached electrodes. The sound processing circuitry of sound processing device 1431 would separate the sound into multiple channels associated with the multiple receivers 1432 implanted in the cochlea; the multiple channels of information would then be encoded into the transmitted ultrasound signal through an appropriate modulation technique. Thus, the transmitted modulated ultrasound signal will comprise an energy part to provide power to the implanted circuitry and an information part to provide signal content to multiple receivers. Implanted receiver 1432 contains both an ultrasound receiving transducer and the necessary electronic circuitry to convert the acoustic energy into electrical power, to demodulate the signal content within the ultrasound signal into one or multiple signal channels, and one or multiple circuits to process the signal content and apply the product to the electrodes 1434 which are disposed on the individual receiver-stimulator, each of the receiver-stimulators disposed within the cochlea It can be appreciated form FIGS. 14a, 14b, and 14c that alternatively (not shown) a controller-transmitter could be implanted in a subcutaneous space and that the sound processing system would communicate via RF, electromagnetic, or acoustic means to initiate ultrasound transmission from the controller-transmitter to the receiver-stimulator.

FIGS. 15a and 15b show more functional details of the system described above and shown in FIGS. 14a-14c. These are similar to the devices shown in FIG. 1, except that they are adapted for cochlear stimulation. In FIG. 15a the sound processing and controller-transmitter device 1541 comprises: a battery 1510, a microphone 1511, sound amplifier and conditioning circuitry 1512, a sound processor and control and timing module 1514, an ultrasound amplifier 1515, and an ultrasound transducer 1516. The battery 1510 which provides power for the sound processing and controller-transmitter device may be of a type commonly used in CIS devices such as a lithium iodine cell or which is optionally a rechargeable battery. The microphone 1511 is used to detect ambient sound. Sound pick-up is connected to sound amplifier and conditioning circuitry 1512 and used by the circuitry to adjust delivery of stimulation. Sound characteristics would be processed into an associated stimulation therapy by the sound processor and control and timing module 1514. Device parameters would include adjustments to transmission frequency, power amplitude, pulse duration, duty cycle, electrode selection, and the like in order to correlate ambient sound into a stimulation therapy. The sound processor and control and timing module 1514 uses device parameters in conjunction with the acquired sound to generate the required control signals for the ultrasound amplifier 1515 which in turn applies electrical energy to the ultrasound transducer 1516 which in turn produces the desired acoustic beam. Ultrasound transducer 1516 is made of piezoelectric ceramic material, a piezoelectric single crystal, or piezoelectric polymer or copolymer films suitable for generating sufficient acoustic energy. It should be appreciated that the functional elements of the sound processing and controller-transmitter device 1541 could be encased in multiple enclosures and connected appropriately with direct wire connections or through communication via RF, electromagnetic, or acoustic signaling.

Referring to FIG. 15b, the receiver-stimulator device 1542, implanted in the path of the acoustic beam, contains an ultrasound transducer 1520, an electrical circuit 1521, and electrodes 1522. Ultrasound transducer 1520, typically made of a piezoelectric ceramic material, a piezoelectric single crystal, or piezoelectric polymer or copolymer films, intercepts a portion of the transmitted acoustic energy and converts it into an electrical current waveform from the original alternating nature of the applied ultrasound pressure wave. This electrical signal is applied to an electrical circuit 1521 which may be one of a type commonly known as an envelope detector, and which may have one of many known circuit configurations, for example a full-wave rectifier, a half-wave rectifier, a voltage doubler or the like. Electrical circuit 1521 produces a voltage pulse with amplitude proportional to the amplitude of the transmitted ultrasound burst and with a pulse length generally equal to the length of the transmitted burst. The circuit 1521 may also be of different configurations and function, and provide output signals having characteristics other than a pulse. This signal is then applied to electrodes 1522, which are typically made of platinum, platinum-iridium, gold, or the like. These may be incorporated onto the outer surface of the device and thus in direct contact within the cochlea. Alternatively, the electrodes 1522 are connected via wires/leads to a main body that consists of the transducer 1520 and electrical circuit 1521 and the electrodes 1522 are adapted to be shapeable, malleable configurations that conform to the structure of the cochlea. Electrodes may be adapted that are round, long, segmented, etc. to increase surface area or to control current density at the electrode. Electrodes may be placed along portions of the cochlea in linear alignment with the cochlea or in any arrangement suitable for the size and location of the regions of the cochlea targeted as a stimulation site. The receiver-stimulator device 1542 is also enclosed within a sealed case 1523 of biologically compatible material Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method for stimulating tissue, comprising:
   transmitting acoustic energy and signal information using an acoustic controller-transmitter;
   receiving said acoustic energy and signal information by an implantable acoustic receiver-stimulator having electrode assembly adapted to be in direct contact with the tissue;
   converting the received acoustic energy to electrical energy by the receiver-stimulator to provide electrical stimulation output to the tissue;
   sensing the electrical stimulation output of the receiver-stimulator using one or more sensors disposed on an external surface of the controller-transmitter, and
   adjusting acoustic transmission from the acoustic controller-transmitter based on the sensed electrical stimulation output in order to compensate for changes in the electrical stimulation output.

2. The method of claim 1, wherein the tissue is chosen from the list of bone, spine, nerves, gastrointestinal tract, brain or cochlea.

3. The method of claim 1, wherein the controller-transmitter operation is controlled by the patient.

4. The method of claim 1, wherein the controller-transmitter is programmed to treat continuous pain.

5. The method of claim 1, wherein the tissue is the nerve.

6. The method of claim 5, where stimulating the nerve treats one or more medical conditions chosen from the list comprising headache, facial pain, pelvic pain, heart failure, hypertension, obesity, migraine, neuropsychiatric disorders, urinary, gastrointestinal, urge or stress urinary incontinence, and fecal incontinence.

7. A system for stimulating tissue, comprising:

an acoustic controller-transmitter comprising one or more sensors disposed on an external surface of the controller-transmitter; and an implantable acoustic receiver-stimulator having an electrode assembly adapted to be in direct contact with the tissue;

wherein the controller-transmitter is adapted to transmit acoustic energy and the receiver-stimulator is adapted to receive acoustic energy and convert said acoustic energy to electrical energy, and the receiver-stimulator is configured to provide electrical stimulation output to the tissue;

wherein the controller-transmitter is configured to periodically sense the electrical stimulation output of the receiver-stimulator using the one or more sensors and adjust acoustic energy transmission accordingly in order to compensate for changes in the electrical stimulation output of the receiver-stimulator.

* * * * *